United States Patent [19]
Russell et al.

[11] Patent Number: 6,030,624
[45] Date of Patent: Feb. 29, 2000

[54] MUCOSAL IMMUNOGENS FOR NOVEL VACCINES

[75] Inventors: Michael William Russell; Georgios Hajishengallis; Susan K. Hollingshead, all of Birmingham; Hong-Yin Wu, Hoover; Suzanne Mary Michalek, Birmingham, all of Ala.

[73] Assignee: UAB Research Foundation, Birmingham, Ala.

[21] Appl. No.: 08/912,180

[22] Filed: Aug. 15, 1997

Related U.S. Application Data

[60] Provisional application No. 60/024,074, Aug. 16, 1996, abandoned.

[51] Int. Cl.$^7$ .......................... A61K 39/02; A61K 39/09; C12N 1/21

[52] U.S. Cl. .................. 424/200.1; 424/93.2; 424/244.1; 435/252.3; 435/252.8

[58] Field of Search .............................. 435/320.1, 252.3, 435/252.33, 252.8; 530/69.3, 350, 403; 424/192.1, 197.11, 200.1, 236.1, 244.1, 261.1, 93.2

[56] References Cited

PUBLICATIONS

Hajishengallis et al. Journal of Immunology 154 (9): 4322–32, May 1, 1995.
Redman et al. Infection and Immunity 63 (5): 2004–2011, May 1995.

*Primary Examiner*—Mary E. Mosher
*Attorney, Agent, or Firm*—Benjamin Aaron Adler

[57] ABSTRACT

The present invention provides chimeric proteins such as Salivary Binding Protein (SBR) coupled to the B subunit of cholera toxin. Such a chimeric protein, when expressed in attenuated *Salmonella typhymurium* produces significant increases in serum IgG and salivary IgA antibody levels after oral immunization. In another embodiment of the present invention, the recombinant plasmid contains a salivary binding protein-cholera toxin A2/B chimeric protein expressed in *E. coli*. Intragastric immunization of SBR coupled to CTB in this chimeric protein form leads to increased antigen responsive T cells. In another embodiment of the present invention, the recombinant plasmid contains a salivary binding protein-cholera toxin$^{AA1}$ chimeric protein expressed in *Salmonella typhimurium*. Oral immunization using this recombinant plasmid results in increased serum IgG responses to antigen. Oral immunization using this recombinant plasmid also resulted in increased salivary IgA antibody responses to antigen.

11 Claims, 26 Drawing Sheets

MUCOSAL IMMUNOGENS FOR NOVEL VACCINES

CROSS REFERENCE TO RELATED APPLICATION

The present application claims priority to provisional application U.S. Ser. No. 60/024,074, filed Aug. 16, 1996, now abandoned.

BACKGROUND OF THE INVENTION

1. Field of the Invention

The present invention relates generally to the fields of molecular immunology and protein chemistry. More specifically, the present invention relates to a novel mucosal immunogens for use in novel vaccines.

2. Description of the Related Art

An oral immunization strategy is when the desired mucosal immunogen is genetically fused to the A2 subunit of cholera toxin (CT) that mediates association with the B subunit of CT, a potent immunoenhancing agent. An antigen selected for evaluating the oral immunogenicity of such non-toxic CTA2/B-based constructs is the saliva-binding region (SBR) of the AgI/II adhesin from the oral bacterium *Streptococcus mutans*. The SBR genetically linked to CTA2/B, designated SBR-CT$^{AA1}$, was found to be immunogenic by the oral route and elicited high levels of secretory immunoglobulin A (S-IgA) and serum IgG antibodies to AgI/II.

Despite its great importance for mucosal defense, the S-IgA antibody response is often of relatively short duration, lasting from a few weeks in experimental animals to a few months in humans. Moreover, whether the secretory immune system is capable of anamnestic immune responses has been debated, but recent studies in mice and humans have addressed the concept of immunological memory at the mucosal surfaces. Immunological memory can be manifested as a long-lasting immune response or as a faster and more vigorous anamnestic response to re-encounter with an antigen. A desirable vaccine characteristic is the induction of prolonged immune responses, especially when the pathogenic organism is frequently encountered at mucosal surfaces, in which case a continuing level of immunity may be necessary.

IgA antibodies in external secretions protect mucosal surfaces, e.g., of the gastrointestinal and respiratory tracts, by blocking microbial adherence and colonization. Oral administration of vaccines can result in the induction of secretory immune responses after uptake of the antigen by the gut-associated lymphoid tissues, a major IgA inductive site. However, most soluble proteins are not only poor immunogens when given orally but they may induce a state of systemic unresponsiveness known as "oral tolerance". The experimental use of cholera toxin from *Vibrio cholerae* or the related heat-labile enterotoxin from *Escherichia coli* as mucosal adjuvants inhibit induction of oral tolerance and potentiates the immune responses to co-administered protein antigens.

Another strategy to overcome problems associated with oral immunization (e.g., denaturation of the protein immunogens by gastric acid and digestive enzymes, limited absorption by the intestinal mucosa, and clearance by peristalsis) as well as the need to purify a vaccine protein, involves the use of avirulent derivatives of *Salmonella typhimurium* as a vaccine delivery system with tropism for the gut-associated lymphoid tissues. Oral immunization with avirulent *S. typhimurium* expressing heterologous antigens is generally not associated with suppression but rather with stimulation of protective secretory and serum antibody responses as well as cell-mediated immune responses.

Initial adherence of *Streptococcus mutans* to tooth surfaces appears to be mediated largely by the 167 kDa surface fibrillar adhesin known as AgI/II (synonyms: antigen B, P1, SpaP, PAc). The adhesion domain that interacts with salivary pellicle has been located to the alanine-rich (A) repeat region in the N-terminal part of the molecule extending from the cell surface probably in an α-helical conformation. Studies on AgI/II indicated that rhesus monkeys immunized with *S. mutans* and protection against dental caries mounted antibody responses especially against the complete molecule rather than against AgII, which corresponds to the C-terminal one-third. These results were supported by the finding that immunization with either complete AgI/II, or the isolated AgI component (corresponding to the N-terminal two-thirds), afforded protection against caries. Thus, one approach to immunization against *S. mutans*-induced dental caries can be based upon the generation of an appropriate antibody response in the saliva that would inhibit the adherence of *S. mutans* to tooth surfaces. Human secretory IgA (S-IgA) antibodies to AgI/II inhibit such adherence. However, S-IgA antibodies in saliva and other secretions are not effectively induced by conventional parenteral immunization.

S-IgA antibodies are most effectively induced by stimulating the common mucosal immune system, for example, by enteric immunization which stimulates the gut-associated lymphoid tissues including the Peyer's patches (PP) of the small intestine. Considerable attention has been given to the development of improved procedures for the oral delivery of vaccines, one of which is coupling antigens to the nontoxic binding B subunit of cholera toxin (CT), a safe and highly immunogenic protein in humans. CTB, because of its avid binding to $G_{M1}$ ganglioside, present on all nucleated cell surfaces, is readily taken up by the M cells covering PP, and passed to the underlying immunocompetent cells which initiate the mucosal IgA antibody response. Antigen-stimulated IgA-committed B cells, and corresponding T helper cells, then emigrate via draining lymphatics to the mesenteric lymph nodes (MLN) and thence via the thoracic duct to the circulation before relocating in the effector sites of mucosal immunity, such as the salivary glands. Terminal differentiation of B cells into IgA-secreting plasma cells occurs here and their product, polymeric IgA is transported through the glandular epithelium to form S-IgA. Other antigens can be coupled to CTB to generate strong mucosal IgA antibody responses to the desired antigen and that intact CT, though toxic, serves as an adjuvant that enhances the response to co-administered antigens.

The expression of foreign genes encoding immunogens of interest in avirulent derivatives of *Salmonella typhimurium* is used as a strategy to induce mucosal immune responses to protein Ags which are usually poor oral immunogens when administered alone. Indeed, *S. typhimurium* appears to be an effective antigen delivery system because of its ability to colonize the gut-associated lymphoid tissue where secretory IgA responses are initiated (1). Electron microscopy studies have shown that *S. typhimurium* preferentially interacts with the specialized antigen-sampling M cells overlying the Peyer's patches in the GALT (2). At these sites, antigenic stimulation of specific IgA-committed B cells results in their migration to mucosal tissues where they differentiate into IgA-secreting plasma cells, with subsequent release of secretory IgA antibodies in external secretions (3). These antibodies play an important role in the defense of mucosal surfaces, e.g., of the gastrointestinal and respiratory tracts, by inhibiting microbial adherence and colonization or invasion (4). Depending on the species and host, Salmonella organisms may disseminate to the spleen, the liver, and regional lymph nodes, take residence in macrophages, and thereby induce serum antibody and cellular immune responses (1).

The issue of whether CTB alone has mucosal adjuvant properties has been questioned especially for oral immunization (14, 19), although CTB confers a targeting property to Ags coupled to it because of its affinity for $G_{M1}$ ganglioside receptors (20). If CTB possesses immunoenhancing properties, other than its carrier/targeting effect, it could also be useful as a Salmonella-expressed adjuvant, especially for proteins that are poor immunogens even when delivered by *S. typhimurium*. A commercially obtained CTB preparation, lacking detectable cAMP-elevating capacity, was found to potentiate in vitro antibody production against an unrelated protein antigen by stimulating the antigen-presenting function of splenic adherent cells through enhanced IL-1 production (21). An enhancing effect on antigen presentation by macrophages was also demonstrated for recombinant (r)CTB (22), which, moreover, up-regulates expression of MHC class II molecules on B cells, which can also act as antigen-presenting cells (23). The fact that commercially available CTB is contaminated with small but variable amounts of intact CT may explain conflicting reports on the adjuvant capacity of CTB (14) as well as findings that commercial CTB is superior to rCTB as an adjuvant for intranasal (i.n.) immunization (24, 25).

The prior art is deficient in the lack of effective mucosal immunogens, for use in, e.g., a caries vaccine. The present invention fulfills this longstanding need and desire in the art.

SUMMARY OF THE INVENTION

The present invention demonstrates that primary oral immunization of mice with a bacterial protein antigen genetically coupled to the A2/B subunits of cholera toxin induced specific secretory immunoglobulin A and serum IgG antibodies that persisted at substantial levels for at least 11 months. A subsequent single booster immunization did not further enhance the antibody responses. Long-term antibody persistence may be especially important in infections caused by common pathogens for which continuous immunity would be advantageous.

The present invention further shows that a major adhesin from the oral pathogen *Streptococcus mutans* is mucosally immunogenic upon genetic fusion with the cholera toxin A2/B subunits. To take advantage of the ability of *Salmonella typhimurium* to deliver cloned antigens to the mucosal inductive sites that would obviate the need for antigen purification, this chimeric construct was expressed in an attenuated *S. typhimurium* strain under the control of bacteriophage T7 transcription. Residual expression of the temperature-regulated T7 RNA polymerase at 30° C. allowed production of the chimeric protein at 2–3% of the total soluble protein, but it was increased 5–6 times following induction at 37° C. Oral administration of a single dose of $10^9$ recombinant Salmonella to mice resulted in serum IgG and salivary IgA antibody responses to Salmonella, cholera toxin, and the streptococcal adhesin, which were generally enhanced after a booster immunization.

The present invention also discloses an avirulent *Salmonella typhimurium* vaccine strain expressing a streptococcal protein adhesin, and a similar clone which produces the same streptococcal antigen linked to the cholera toxin A2/B subunits, which were compared for their ability to induce antibody responses to the expressed heterologous antigen after oral or intranasal immunization of mice. Expression of cloned immunogens in these systems is temperature-regulated, being optimal at 37° C., and the two clones produced similar levels of the streptococcal antigen. Both clones were found to stimulate high levels of serum IgG and mucosal IgA antibodies to the cloned immunogen. A consistent trend was observed towards higher mucosal IgA but lower serum IgG responses in the case of the *S. typhimurium* vector that co-expressed CTA2/B, a potential mucosal adjuvant, regardless of the route of administration. Also noteworthy was the capacity of these antigen-delivery systems to induce anamnestic mucosal and systemic responses to the cloned immunogen 15 weeks after the primary immunization, despite pre-existing immunity to the Salmonella vectors. Although the serum IgG response against the Salmonella vector was characterized by a high IgG2a/IgG1 ratio (indicative of the Th1/Th2 profile), a mixed IgG1 and IgG2a pattern was observed for the carried heterologous antigen, which displayed a dominant IgG1 response when administered as a purified immunogen. The present invention indicates that the recombinant streptococcal antigen and CTA2/B are strong immunogens when expressed by the antigen-delivery system, and that CTA2/B may have an additional immunoenhancing activity in the mucosal compartment besides its ability to target antigen uptake into the mucosal inductive sites and, therefore, may be useful as a *S. typhimurium*-cloned adjuvant for co-expressed protein Ags.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

correspond to the Mr of SBR-CTA2 and CTB (monomer), respectively. The CTB component of purified SBR-CT$^{AA1}$ ran relatively faster (Mr~11.5 kDa) due to processing of the precursor polypeptide by signal peptidase during transport to the periplasmic space, while an additional band from SBR-CTA2 may represent a degradation product.

Figure 4A:
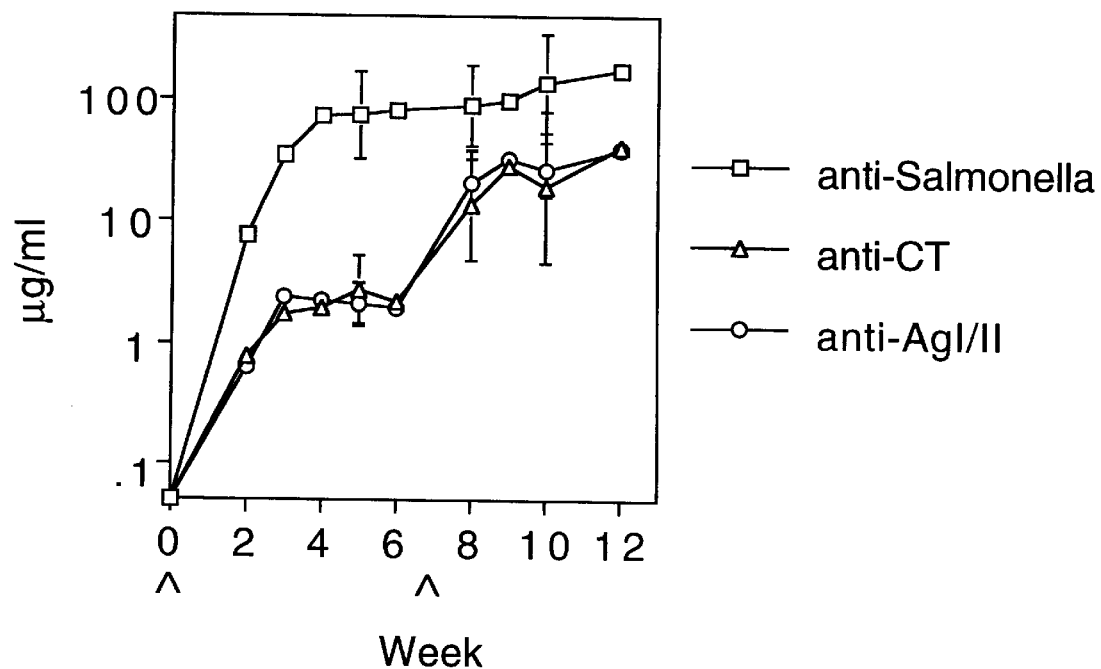
Figure 4B:
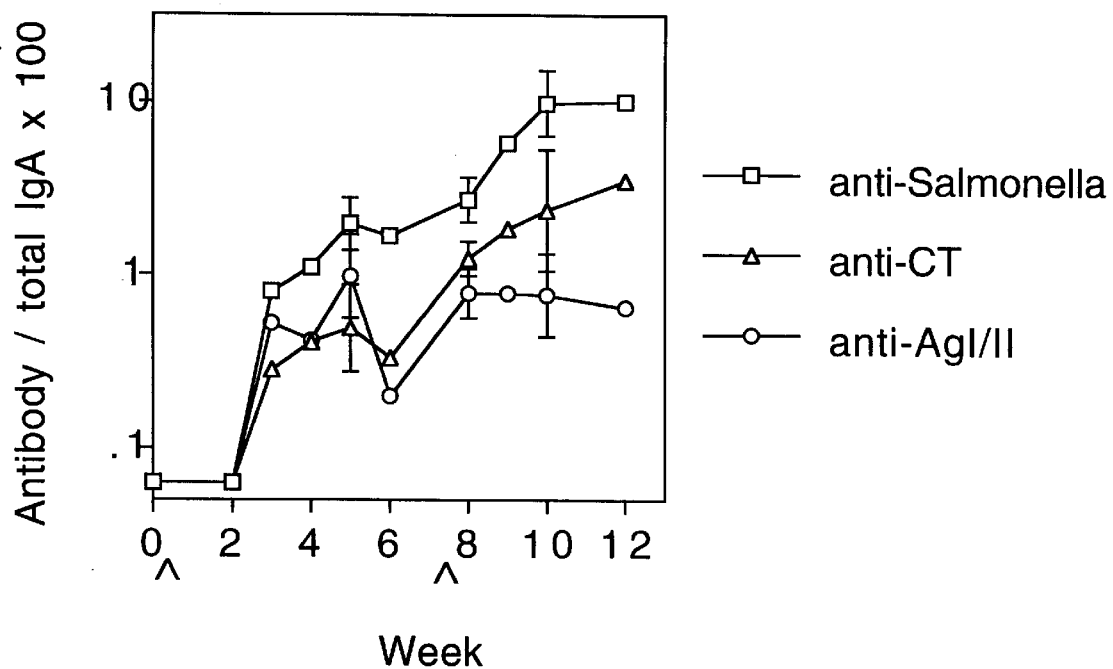

FIGS. 4(A)–4(B) shows the serum IgG FIG. 4A and salivary IgA FIG. 4B antibody responses to S. typhimurium and cloned antigens in mice orally immunized with $10^9$ bacteria on weeks 0 and 7 (^). Immune response data for weeks 5, 8 and 10 represent geometric means x/+ standard deviation of five mice. Pooled samples were assayed at other time points.

Figure 5A:
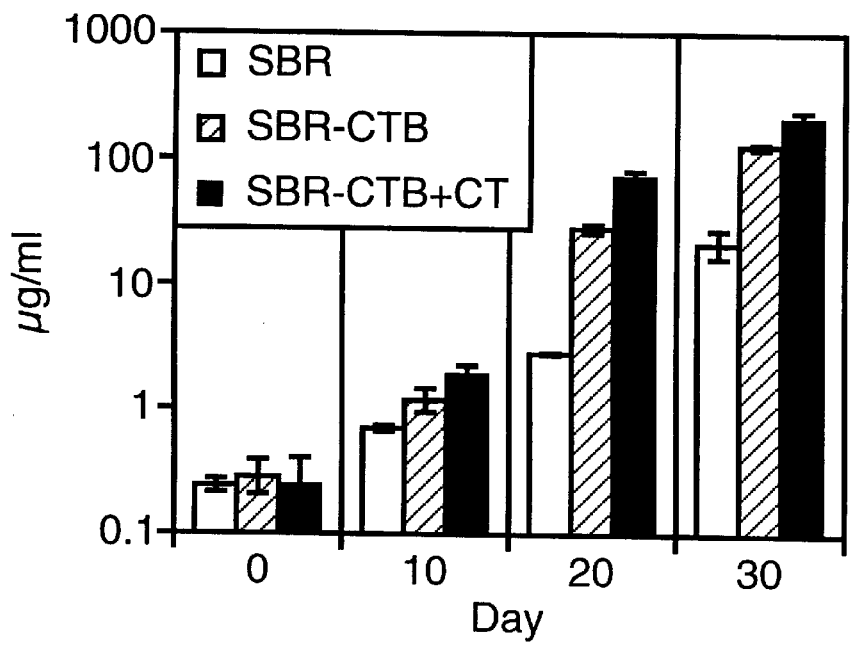
Figure 5B:
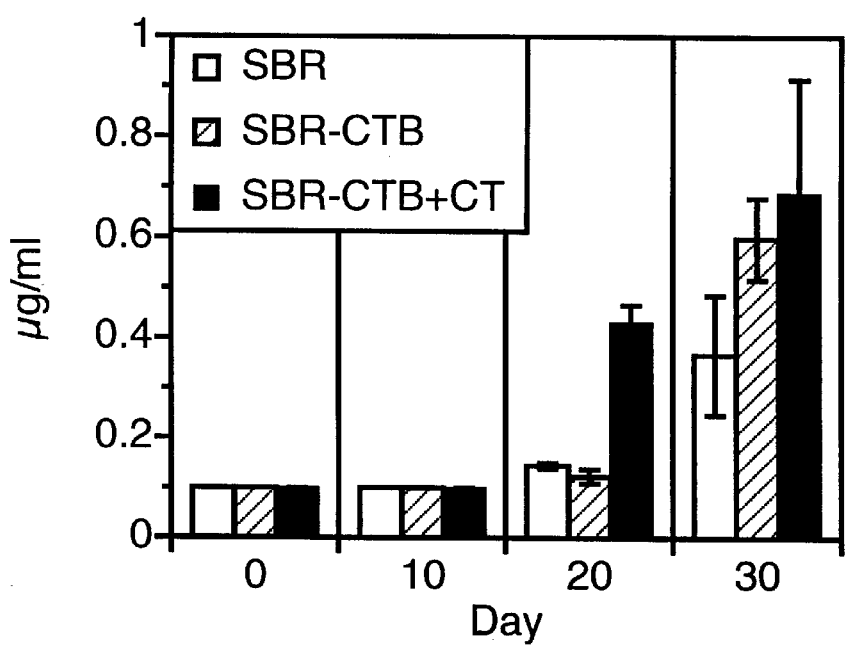

FIGS. 5(A)–5(B) show the serum IgG FIG. 5A and salivary IgA FIG. 5B antibody responses to AgI/II in unimmunized mice and mice immunized once, twice, or three times with SBR, SBR-CTA2/B, or SBR-CTA2/B plus CT adjuvant. Immunizations were given on days 0, 10, and 20, and samples were collected 10 days after each immunization, i.e., on days 0 (unimmunized mice), 10 (one dose), 20 (2 doses), or 30 (3 doses). Results shown are mean+/−SD of samples from 3 animals analysed separately. Salivary IgA antibodies were below detectable levels (<0.1 μg/ml) on days 0 and 10, and are shown at this level in (b).

Figure 6:
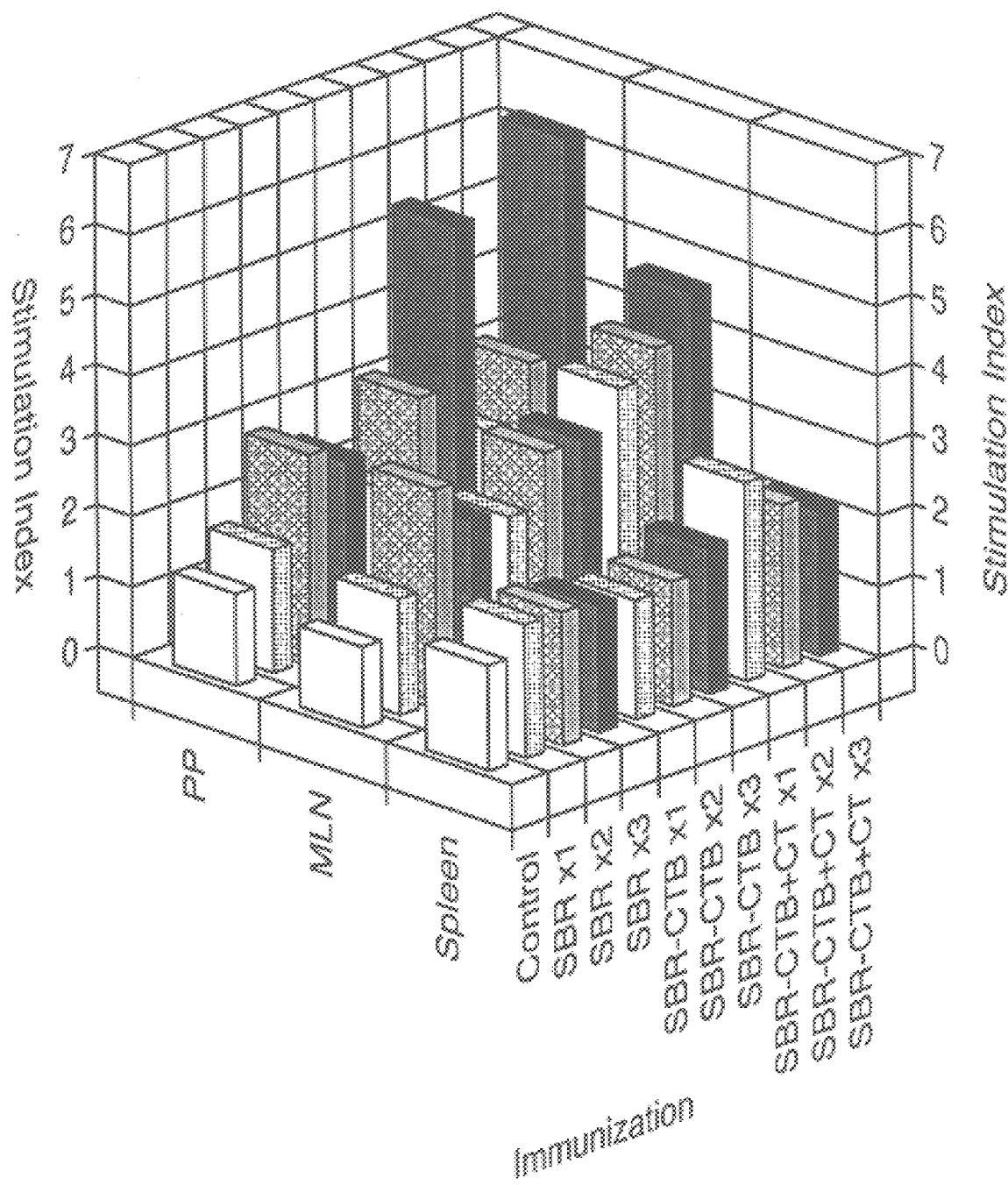

FIG. 6 shows the proliferative responses of cells from PP, MLN, and spleens of unimmunized (control) mice and mice immunized once, twice, or three times with SBR, SBR-CTA2/B, or SBR-CTA2/B plus CT adjuvant, cultured in vitro with AgI/II. Results shown are mean stimulation indices of 3 replicate cultures; SD values ranged from ~0.04 to ~0.95.

Figure 7:
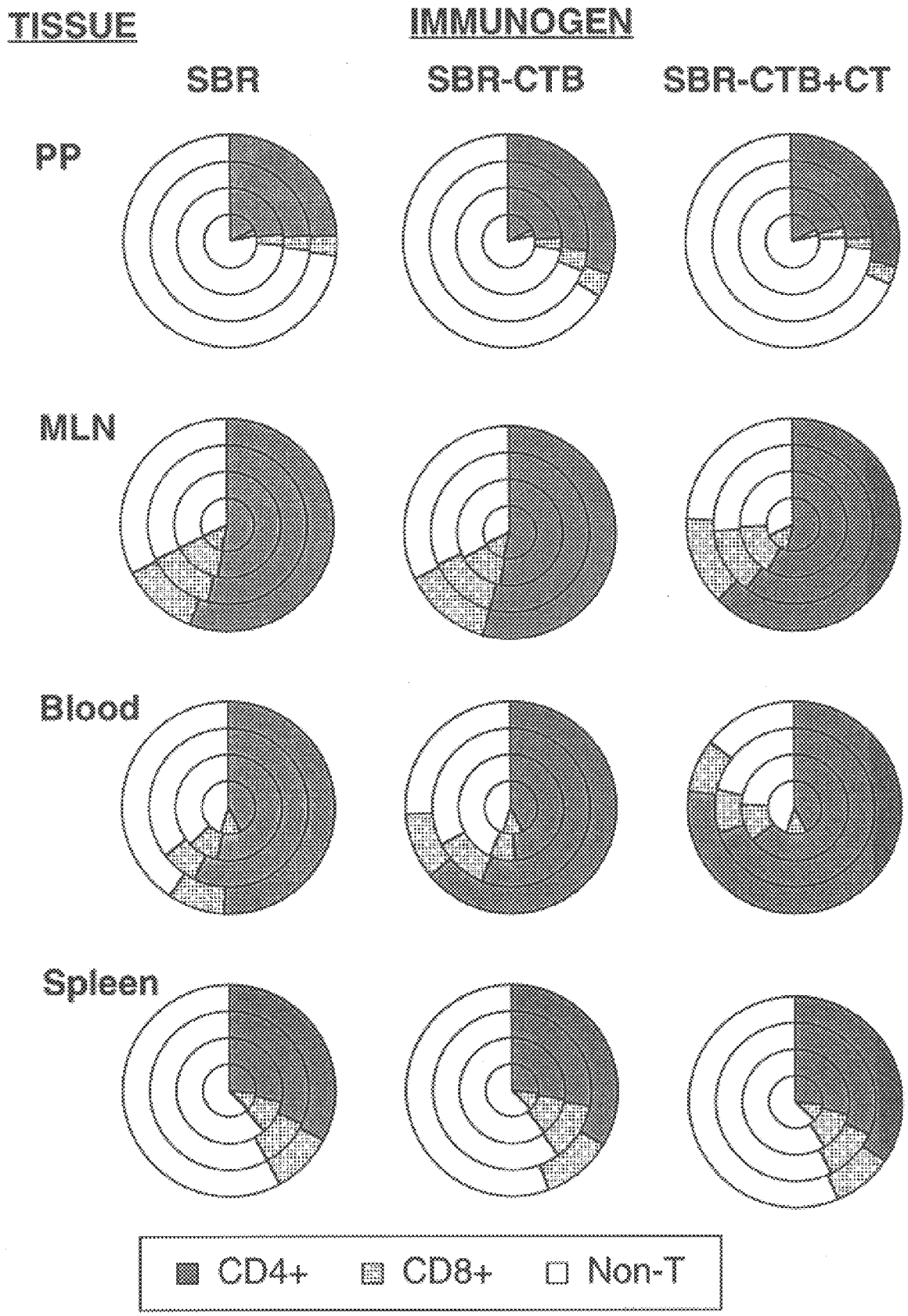

FIG. 7 shows the phenotypic analysis of cells from PP, MLN, peripheral blood, and spleens of unimmunized mice and mice immunized once, twice, or three times with SBR, SBR-CTA2/B, or SBR-CTA2/B plus CT adjuvant. Each 'pie' shows the proportions of CD4$^+$, CD8$^+$, and CD3$^-$ (non-T) cells as a percentage of total gated mononuclear cells determined by flow cytometry, starting with unimmunized mice (center of each 'pie'), and proceeding outwards in concentric rings with mice immunized once, twice, or three times. Numbers within the rings are the % of each phenotype of cells (for clarity, CD8$^+$ cell data are shown outside the 'pies' in descending order: 0, 1, 2, and 3 doses); the value shown for MLN from mice immunized once with SBR (marked as "51?") was not obtained experimentally, but was inserted for plotting purposes as the average of the values either side of it. The numbers in each ring of a 'pie' do not sum to exactly 100%, because of the presence of some CD4$^-$/CD8$^-$ ("double-negative") CD3$^+$ T cells, and possibly some CD4$^+$/CD8$^+$ ("double-positive") T cells in each cell preparation.

Figure 8A:
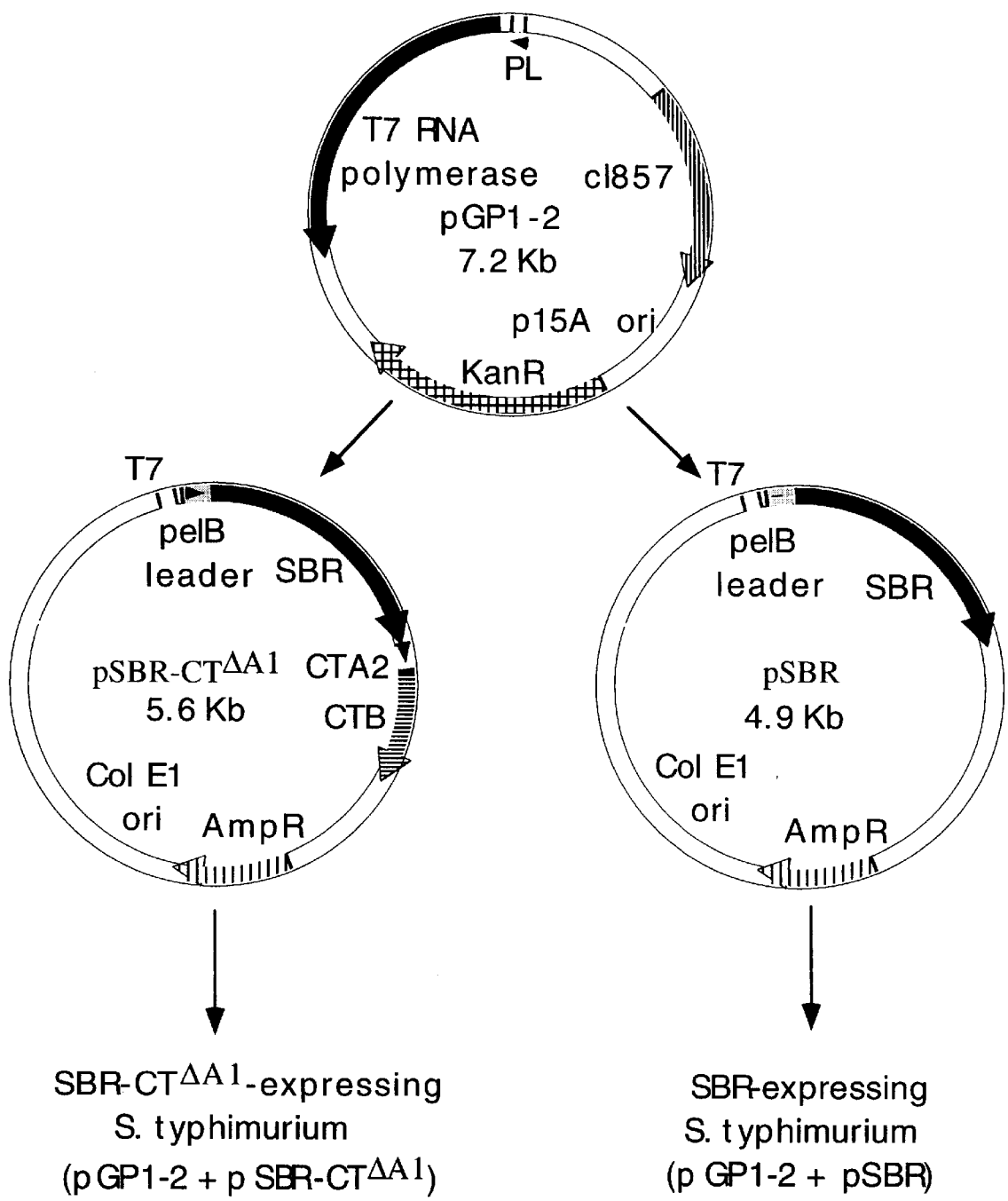
Figure 8B:
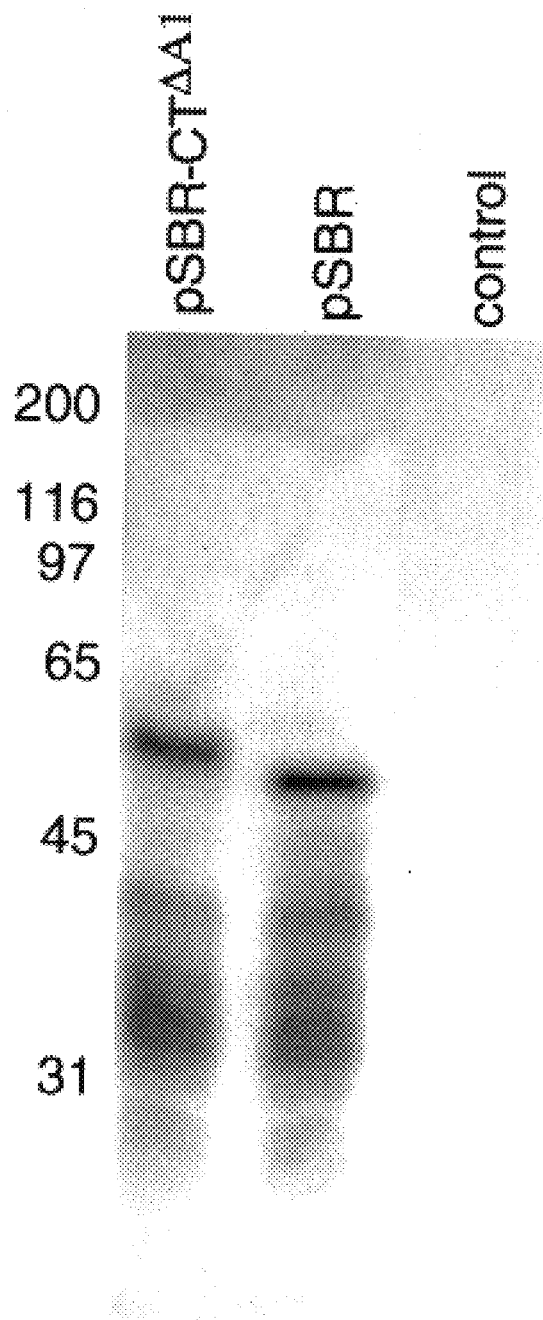

FIG. 8A shows a schematic representation of the plasmids used to transform SBR-CT$^{AA1}$-or SBR-expressing S. typhimurium clones. FIG. 8B shows a western blotting of cell lysates from the SBR-CT$^{AA1}$-and the SBR-producing clones using antibodies to SBR detected the SBR-CTA2 fusion protein and the SBR, respectively. The control lane is a lysate from a clone transformed with the pGP1-2 plasmid only.

Figure 9A:
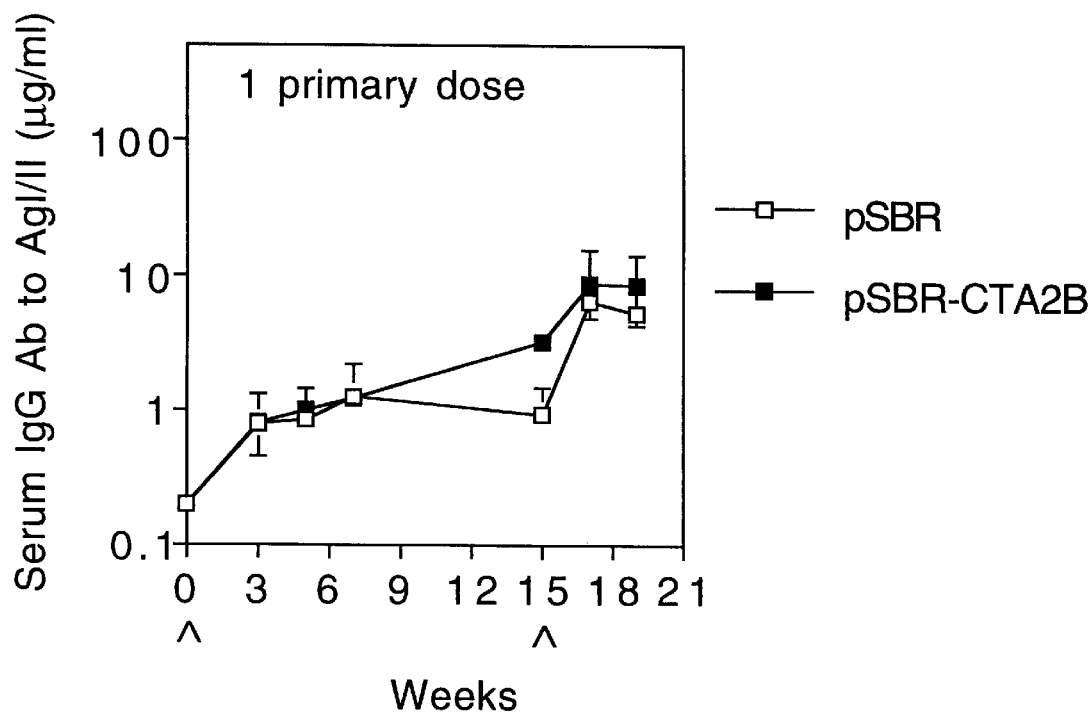
Figure 9B:
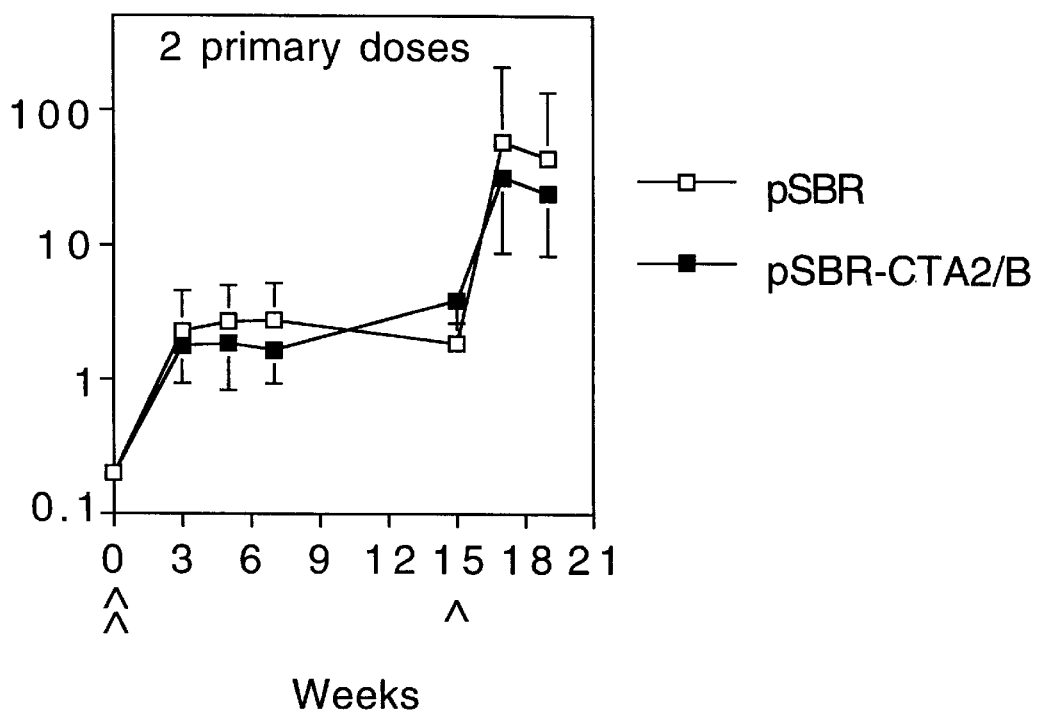
Figure 9C:
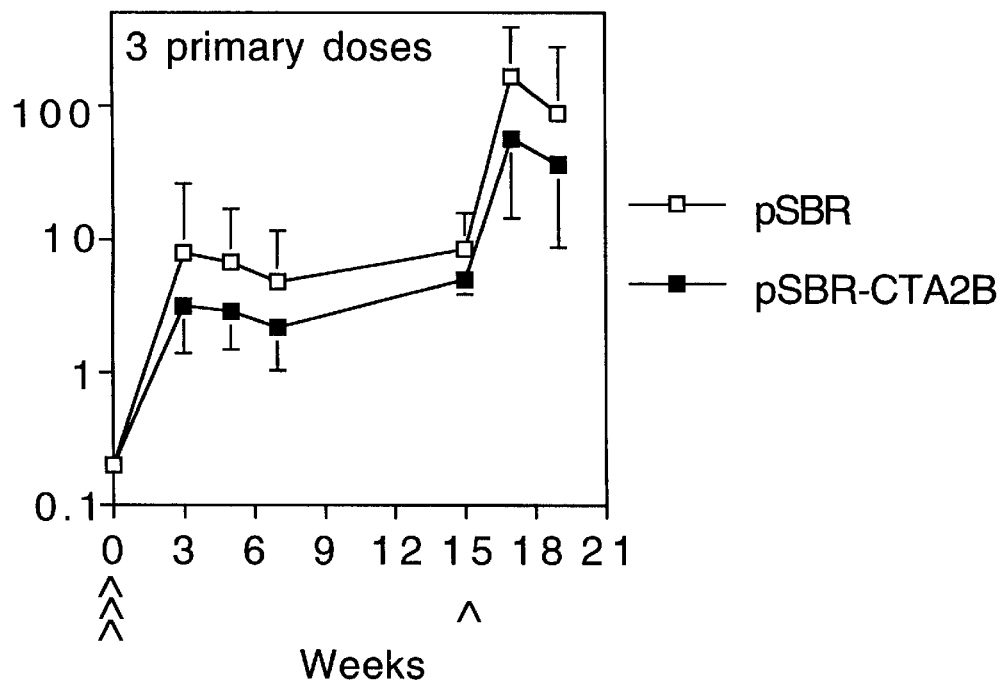

FIGS. 9(A)–9(C) shows the serum IgG antibody responses to native AgI/II in mice orally immunized (^) on weeks 0 and 15 with SBR- or SBR-CT$^{AA1}$-expressing S. typhimurium clones. During week 0 mice were immunized with one FIG. 9A, two FIG. 9B, or three FIG. 9C doses of $10^9$ CFU of the appropriate S. typhimurium clone. At 15 weeks the animals were given a single dose of $10^{10}$ CFU. Data represent geometric means x/(SD of 5 to 6 mice. For clarity only the upper or lower SD bars are shown.

Figure 10A:
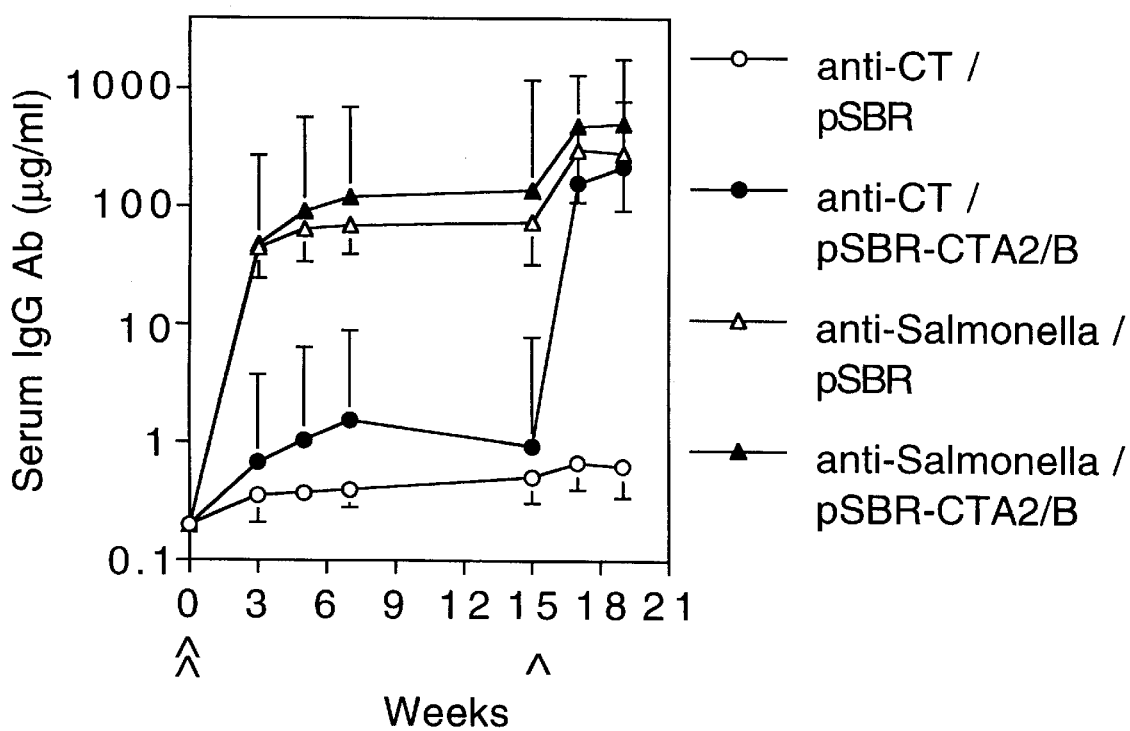
Figure 10B:
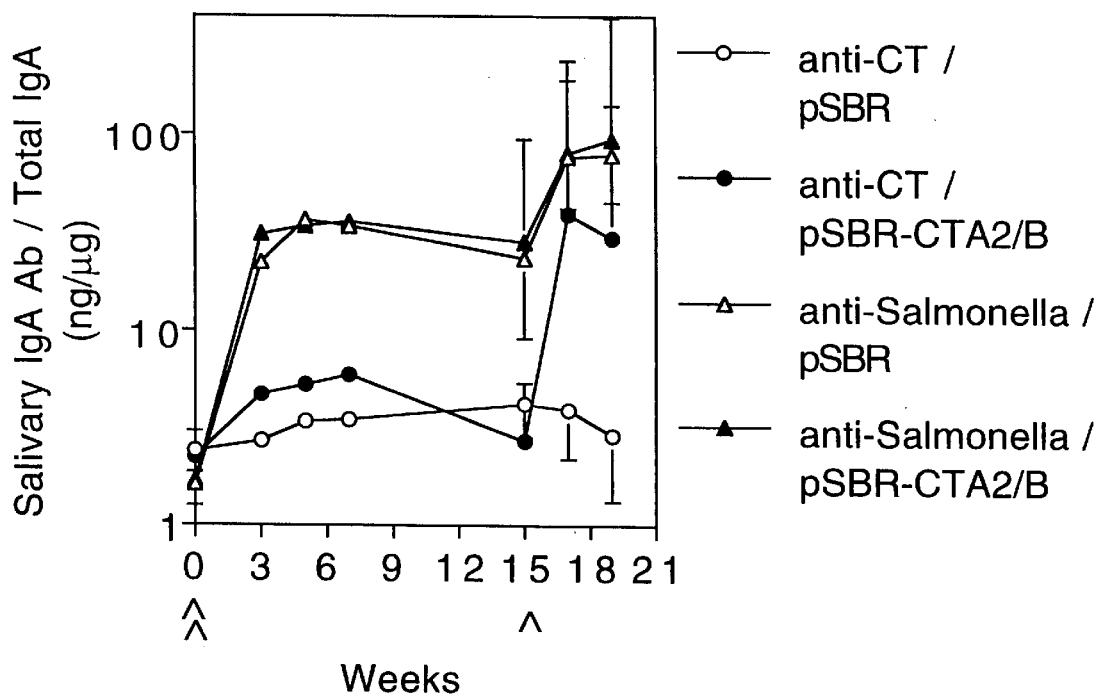
Figure 10C:
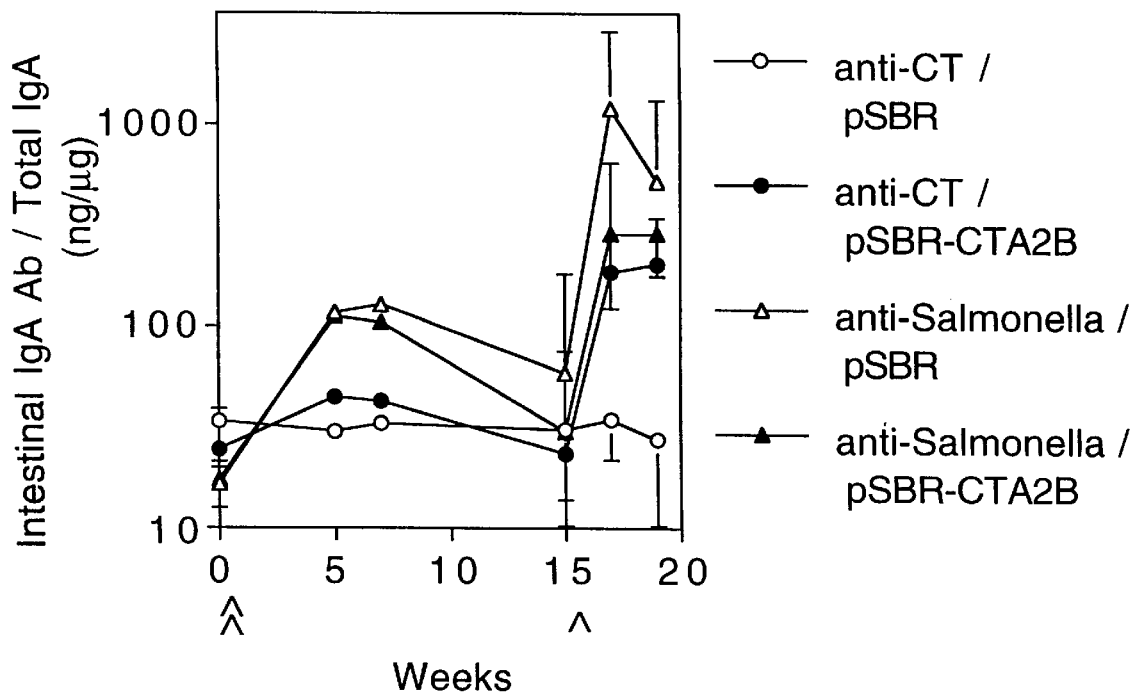

FIGS. 10(A)–10(C) shows the serum IgG (FIG. 10A), salivary IgA (FIG. 10B), and intestinal IgA (FIG. 10C) antibody responses to CT and S. typhimurium vector after oral immunization (^) of mice with SBR- or SBR-CT$^{AA1}$-producing Salmonella clones on weeks 0 and 15. Mice were immunized with two doses of $10^9$ CFU of the appropriate S. typhimurium clone during week 0, and were given a single dose of $10^{10}$ CFU 15 weeks later. Results are shown as geometric means x/÷ SD of 5 to 6 mice. Data for weeks 3 to 7 (FIGS. 10B and 10C) were obtained by assaying pooled samples from 5 to 6 mice per corresponding group. For clarity only the upper or lower SD bars are shown.

Figure 11A:
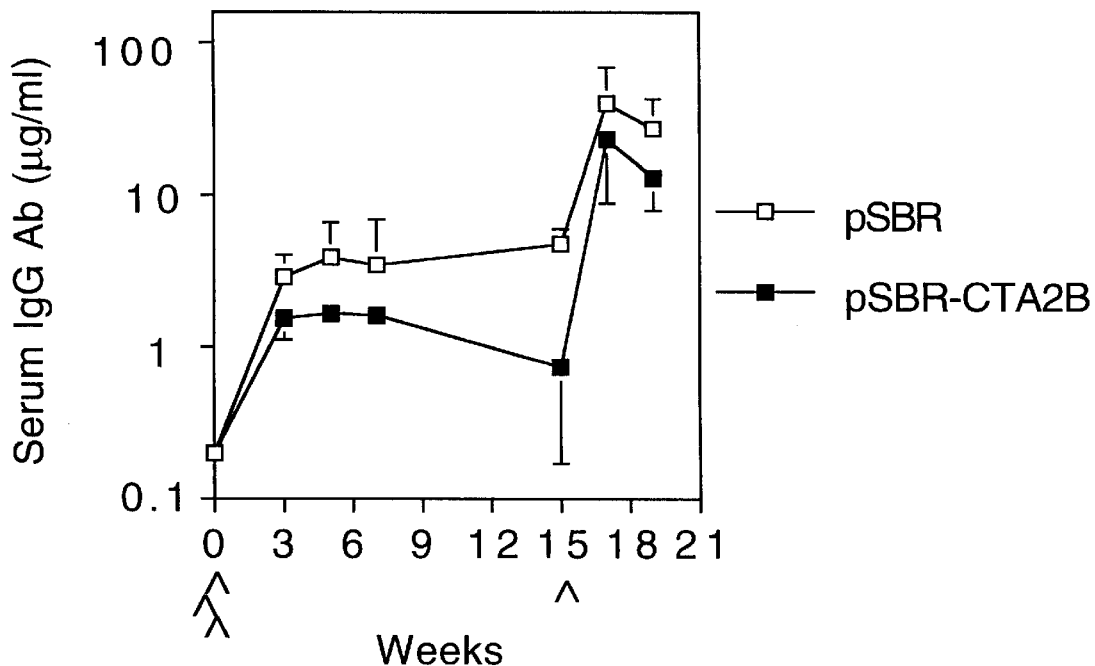
Figure 11B:
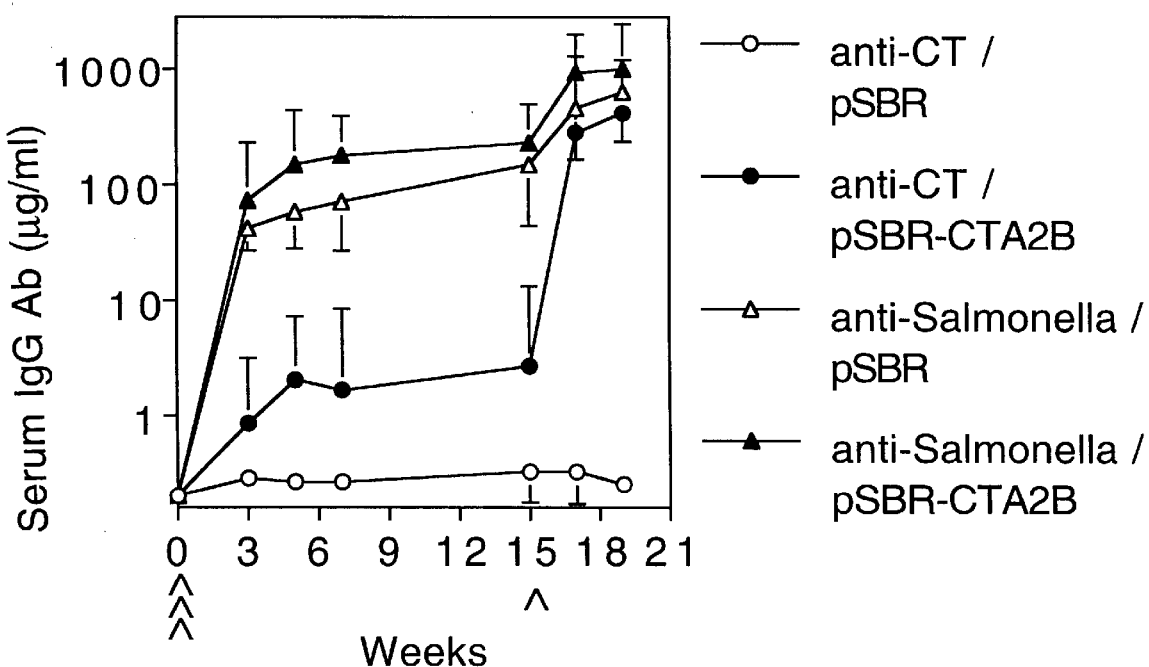

FIGS. 11(A)–11(B) shows the serum IgG antibody responses to AgI/II (FIG. 11A) and CT and Salmonella vector (FIG. 11B) in mice immunized (^) by the i.n. route on weeks 0 and 15 with SBR- or SBR-CT$^{AA1}$-expressing S.typhimurium clones. During week 0 mice were immunized with three doses of $10^8$ CFU of the appropriate S. typhimurium clone and 15 weeks later they were given a single dose of $10^9$ CFU. Data are expressed as the geometric means x/(SD of 6 mice.

Figure 12A:
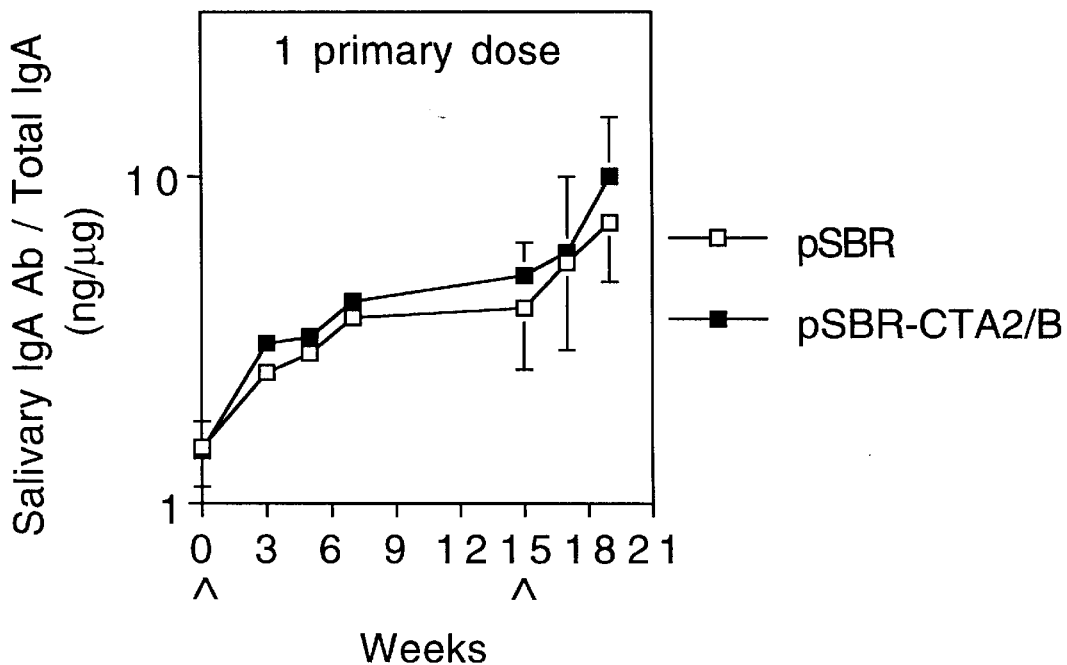
Figure 12B:
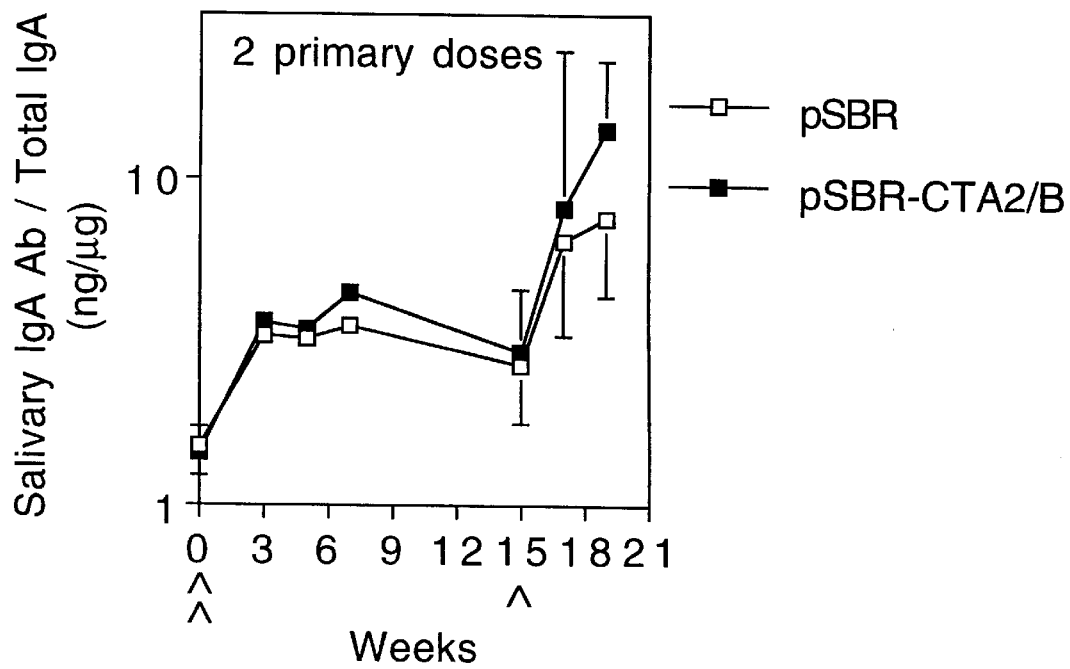
Figure 12C:
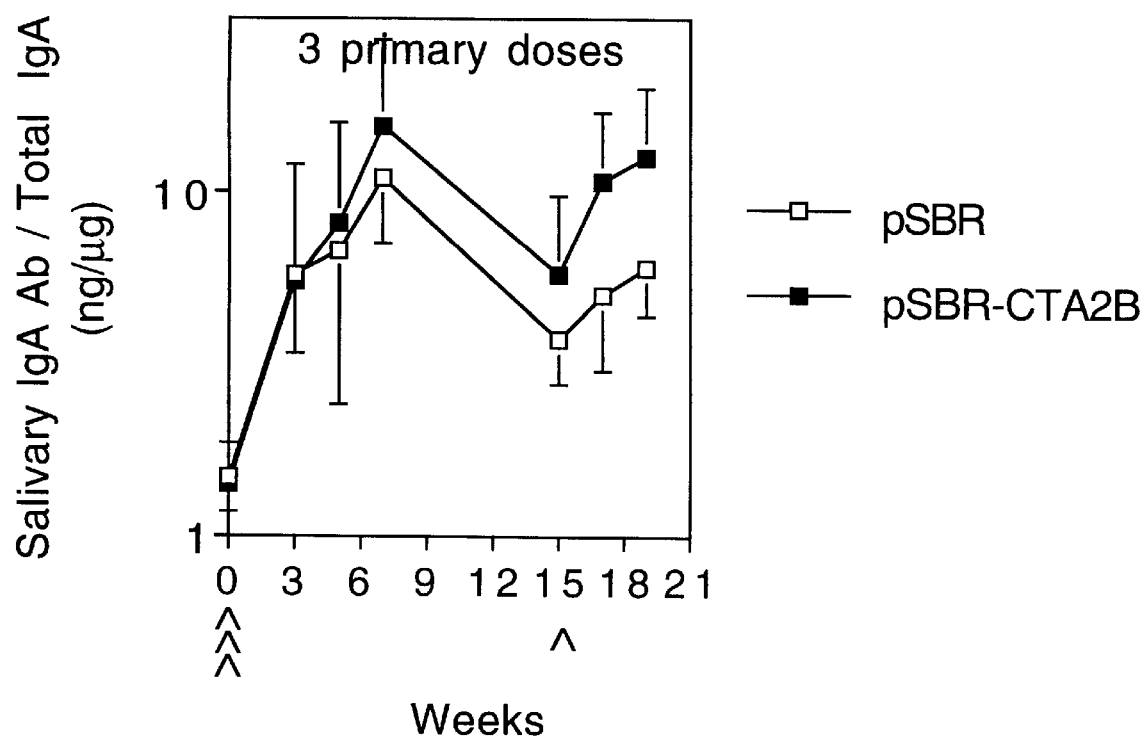

FIGS. 12(A)–12(C) shows the salivary IgA antibody responses to AgI/II in mice orally immunized (^) on weeks 0 and 15 with SBR- or SBR-CT$^{AA1}$-expressing S.typhimurium. During week 0 mice were immunized with one FIG. 12A, two FIG. 12B, or three FIG. 12C doses of $10^9$ CFU of the appropriate S. typhimurium clone. At 15 weeks the animals were given a single dose of $10^{10}$ CFU. Results are the geometric means x/(SD of 5 to 6 mice. Data for weeks 3, 5, and 7 in groups which received one or two primary doses, were obtained by assaying pooled samples from 5 to 6 mice per corresponding group.

Figure 13A:
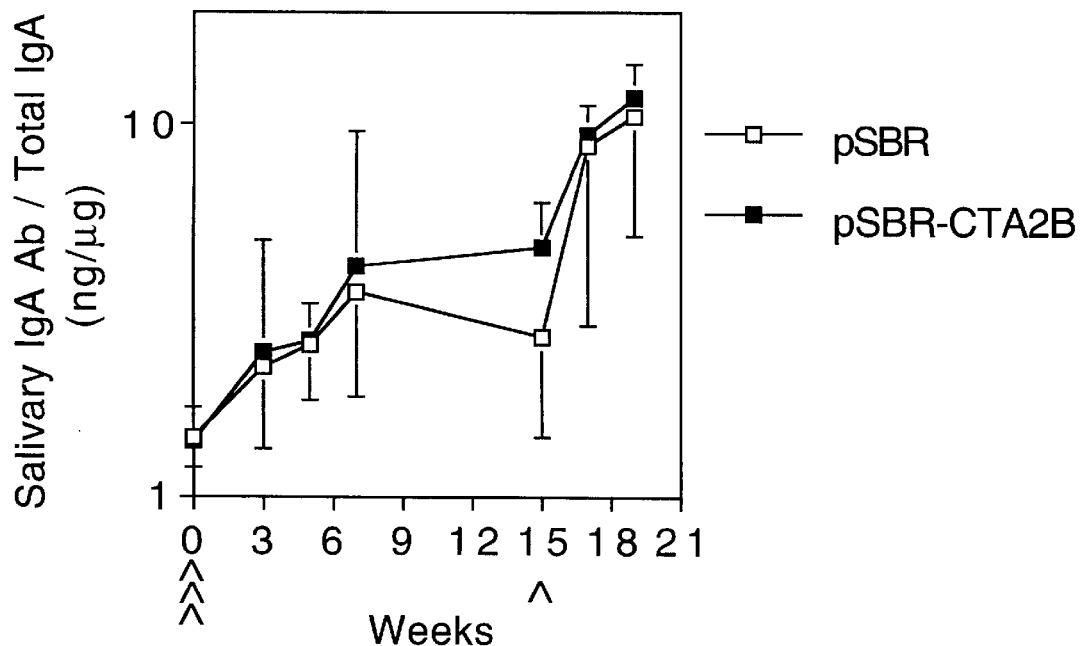
Figure 13B:
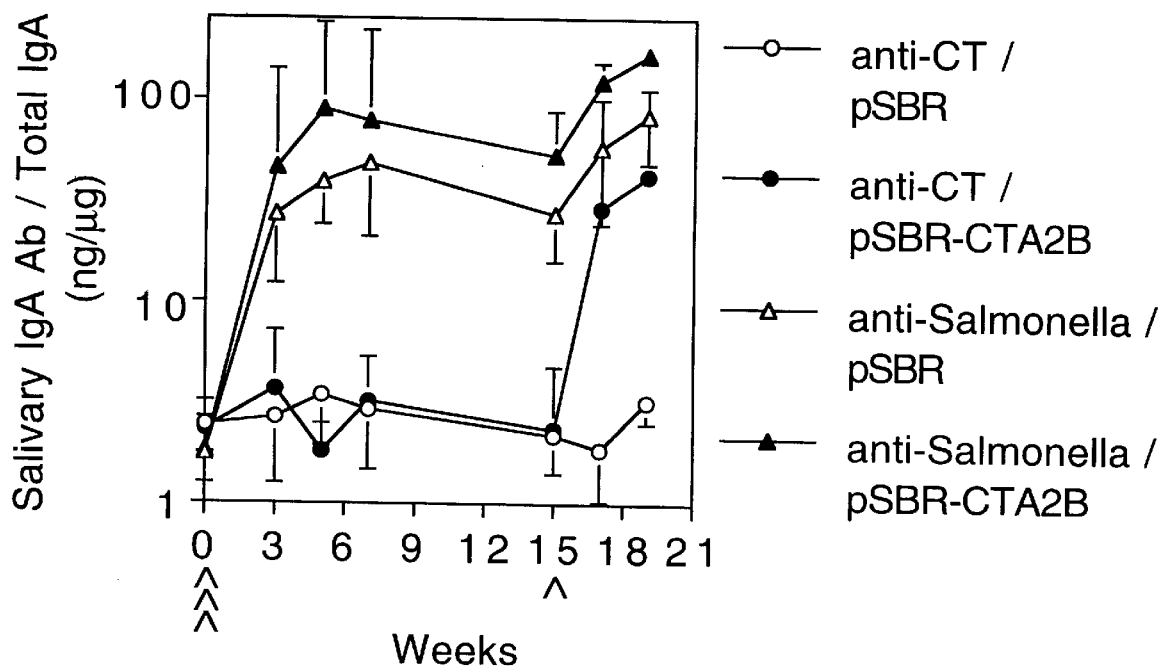

FIGS. 13(A)–13(B) shows the salivary IgA antibody responses to AgI/II (FIG. 13A) and CT and Salmonella vector (FIG. 13B) after i.n. immunization (^) of mice on weeks 0 and 15 with SBR- or SBR-CT$^{AA1}$-expressing S. typhimurium clones. During week 0 mice were immunized with three doses of $10^8$ CFU of the appropriate S. typhimurium clone and 15 weeks later they were given a single dose of $10^9$ CFU. Data represent geometric means x/(SD of 6 mice.

Figure 14A:
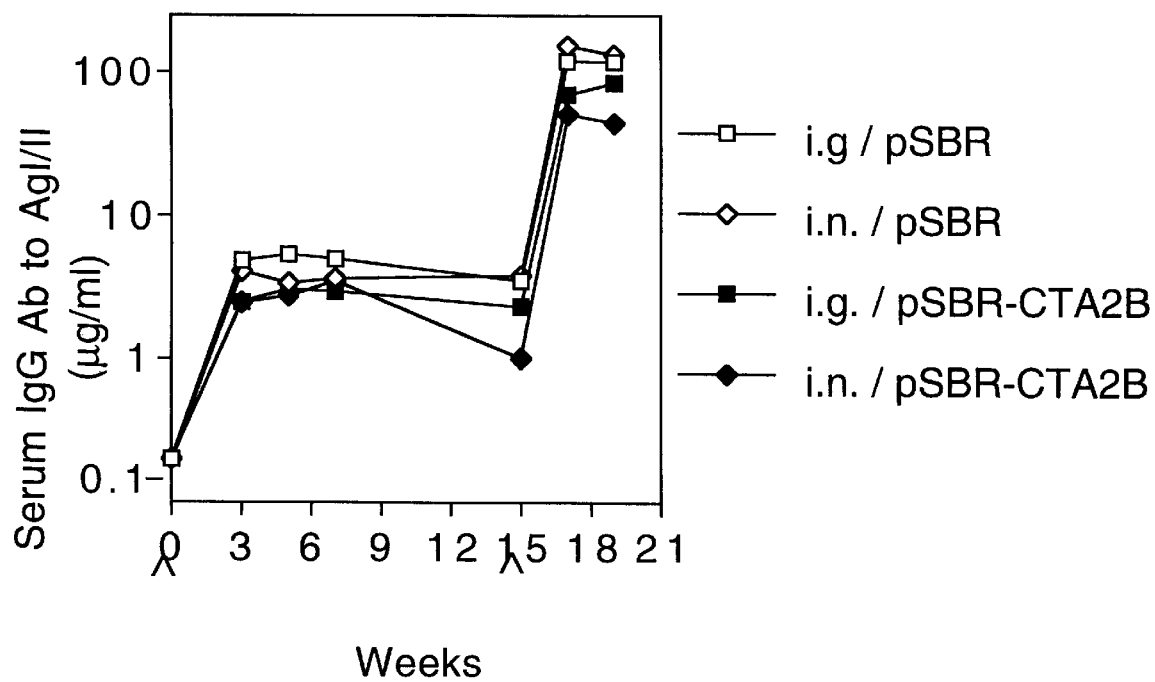
Figure 14B:
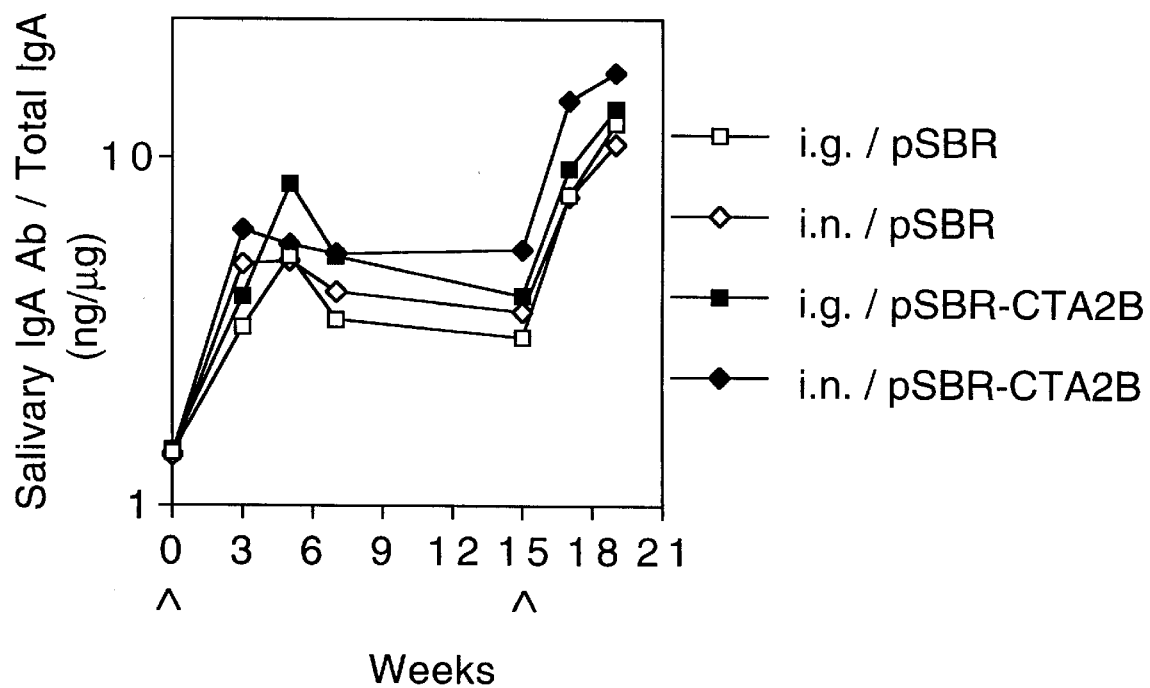

FIGS. 14(A)–14(B) shows the serum IgG FIG. 14A and salivary IgA FIG. 14B antibody levels to AgI/II induced by either i.n. or i.g. immunization (^) of mice on weeks 0 and 15 with S. typhimurium expressing SBR alone or SBR-CT$^{AA1}$ chimeric protein. The animals were given a single primary immunization of $10^9$ CFU (i.n.) or $10^{10}$ CFU (i.g.) followed by a booster immunization with the same dose 15 weeks later. Data were obtained by assaying pooled samples from 3 mice per corresponding group.

Figure 15A:
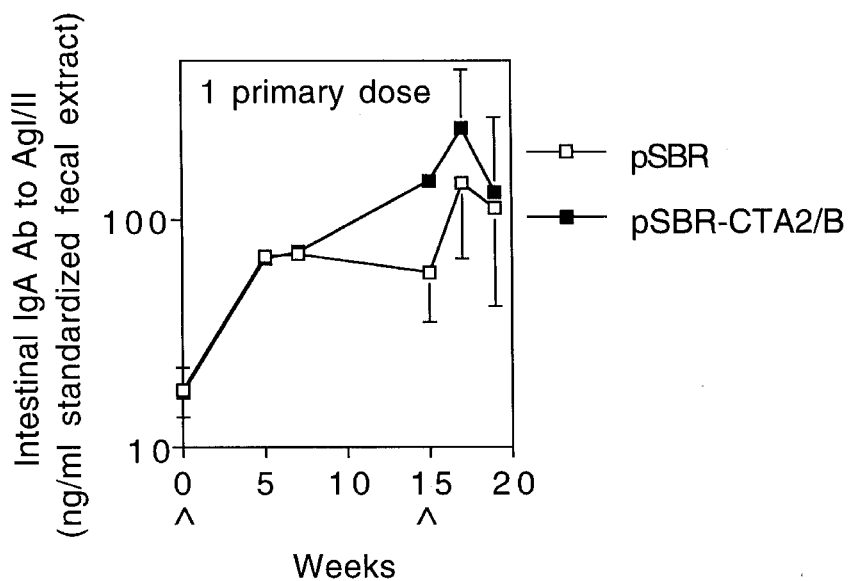
Figure 15B:
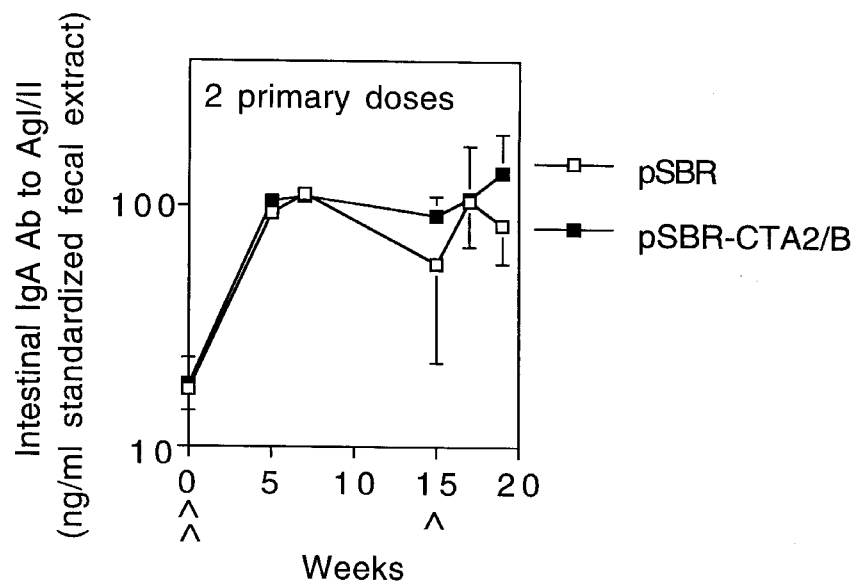
Figure 15C:
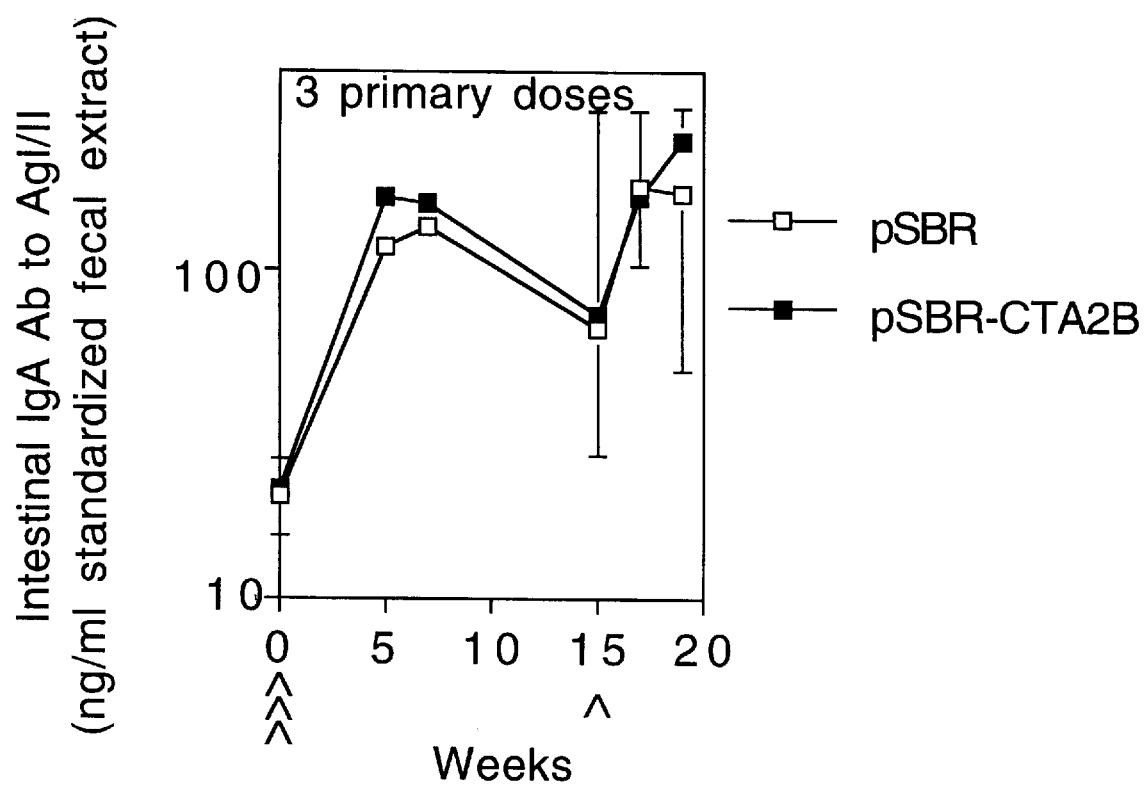

FIGS. 15(A)–15(C) shows the intestinal IgA antibody responses to AgI/II in mice orally immunized (^) on weeks 0 and 15 with S. typhimurium clones expressing SBR or SBR-CT$^{DA1}$. During week 0 mice were immunized with one FIG. 15A, two FIG. 15B, or three FIG. 15C doses of $10^9$ CFU of the appropriate S. typhimurium clone. At 15 weeks the animals were given a single dose of $10^{10}$ CFU. Results are the geometric means x/(SD of 5 to 6 mice. Data for weeks 5 and 7 were obtained by assaying pooled samples from 5 to 6 mice per corresponding group.

Figure 16A:
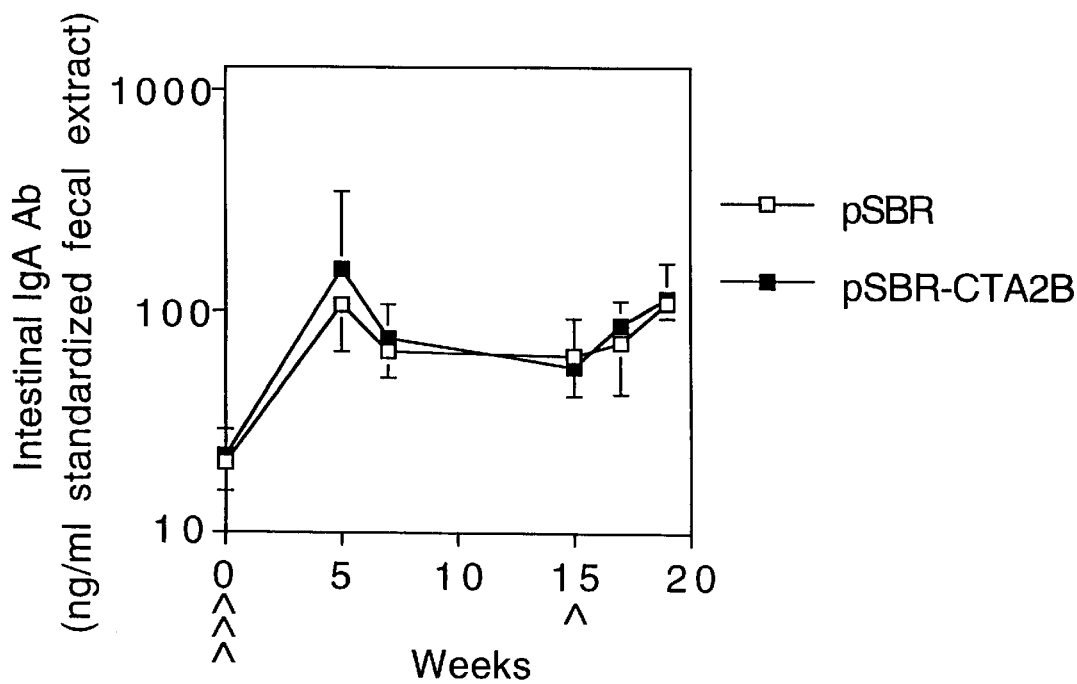
Figure 16B:
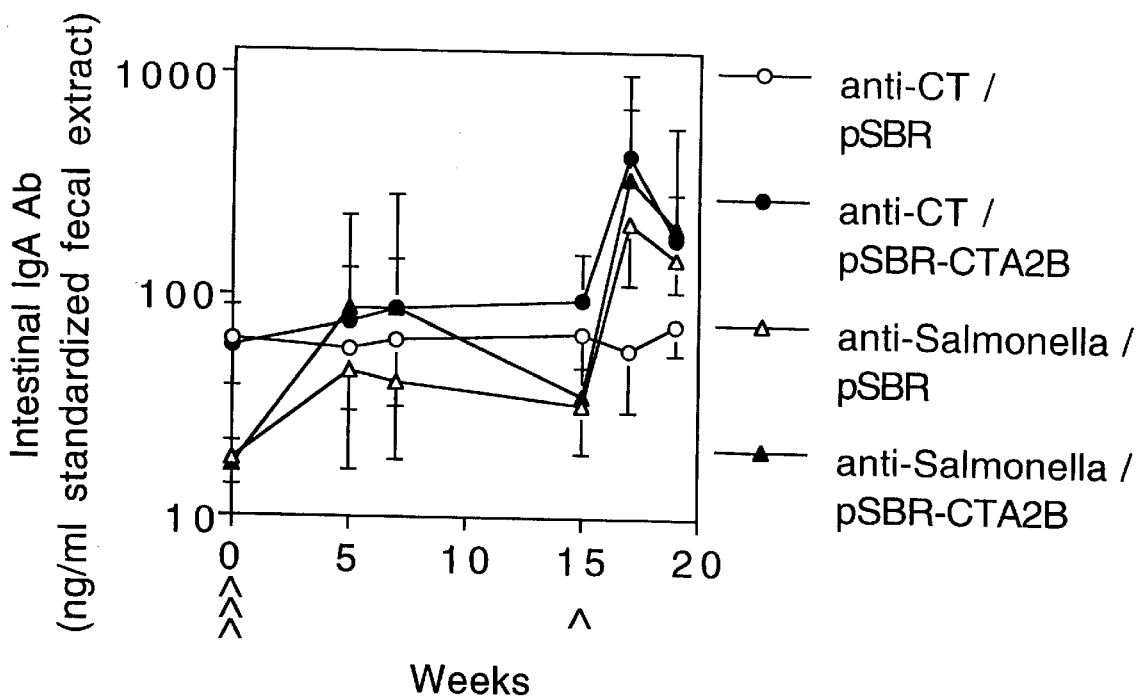

FIGS. 16(A)–16(B) shows the intestinal IgA antibody responses to AgI/II (FIG. 16A) and CT and S. typhimurium (FIG. 16B) after i.n. immunization (^) of mice on weeks 0 and 15 with S.typhimurium vectors producing SBR alone or SBR-CT$^{ΔA1}$ chimeric molecule. During week 0 mice were immunized with three doses of $10^8$ CFU of the appropriate *S. typhimurium* clone and 15 weeks later they were given a single dose of $10^9$ CFU. Data represent geometric means x/(SD of 6 mice.

Figure 17:
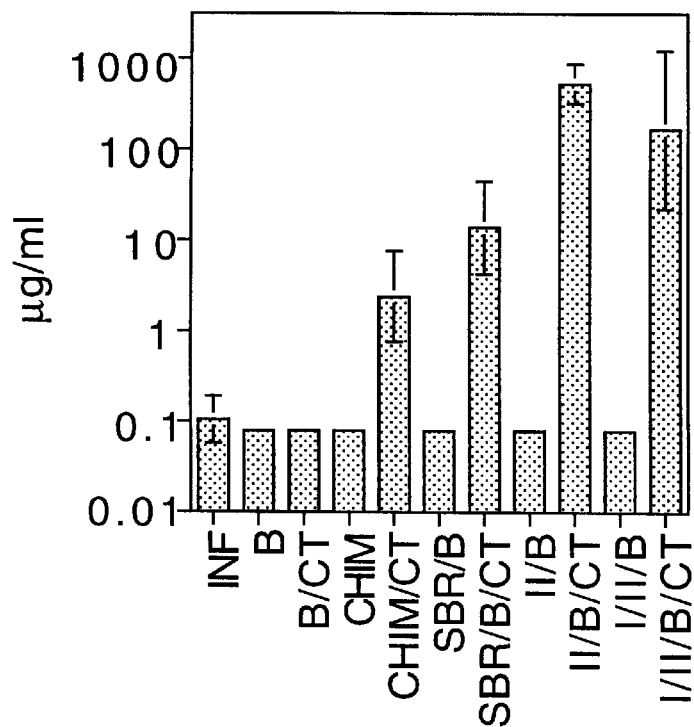

FIG. 17 shows the serum IgG antibody responses to native AgI/II in intranasally immunized rats. The animals were immunized three times at 14-day intervals with 25 μg of recombinant B subunit of cholera toxin (rCTB) or with 50 μg of the appropriate immunogen genetically or chemically linked to rCTB (see group definition) in the presence or absence of an adjuvant amount (1 μg) of cholera toxin (CT). Data are from samples obtained two weeks after the last immunization and represent geometric means±standard deviation (SD).

Figure 18:
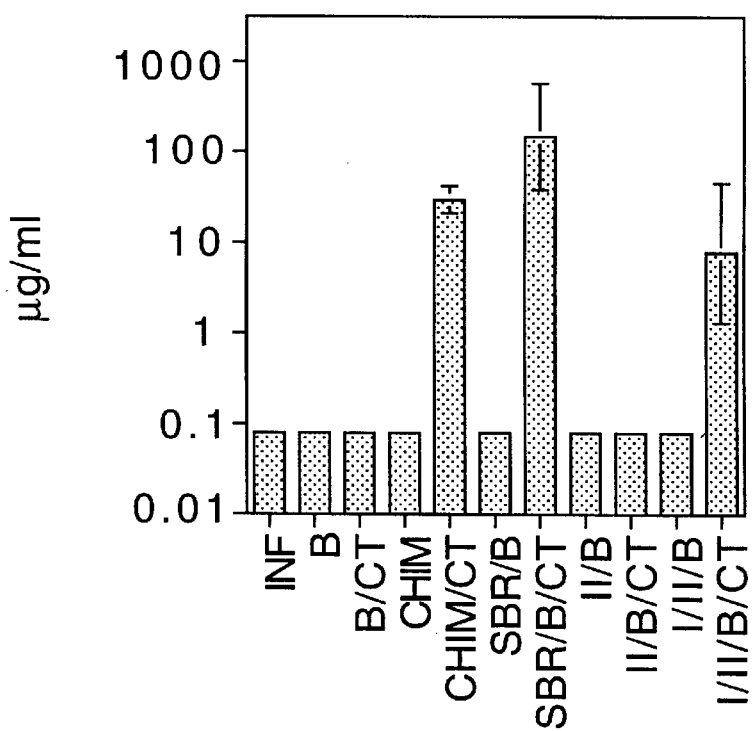

FIG. 18 shows the serum IgG antibody responses to recombinant SBR (42-kDa saliva-binding region at the N-terminal of AgI/II) in intranasally immunized rats. The animals were immunized three times at 14-day intervals with 25 μg of rCTB or with 50 μg of the appropriate immunogen genetically or chemically linked to rCTB (see group definitions) in the presence or absence of an adjuvant amount (1 μg) of CT. Data are from samples obtained two weeks after the last immunization and represent geometric means±SD.

Figure 19:
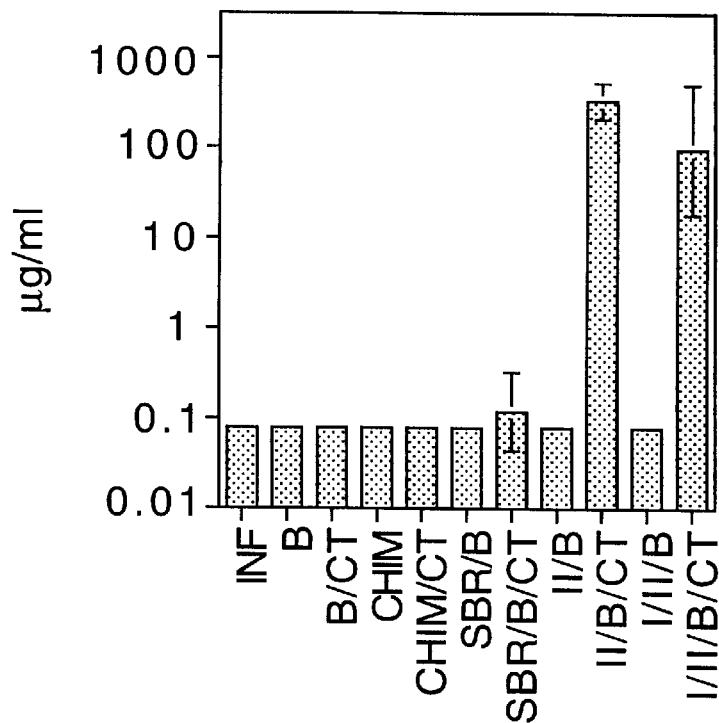

FIG. 19 shows the serum IgG antibody responses to AgII (C-terminal one-third of AgI/II) in intranasally immunized rats. The animals were immunized three times at 14-day intervals with 25 μg of rCTB or with 50 μg of the appropriate immunogen genetically or chemically linked to rCTB in the presence or absence of an adjuvant amount (1 μg) of CT. Data are from samples obtained two weeks after the last immunization and represent means±SD.

Figure 20:
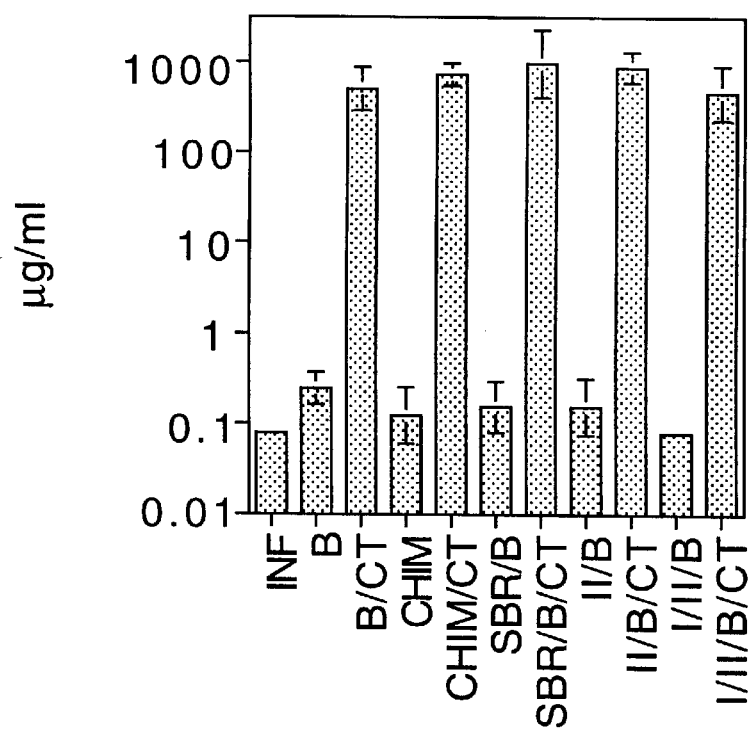

FIG. 20 shows the serum IgG antibody responses to CT in intranasally immunized rats. The animals were immunized three times at 14-day intervals with 25 μg of rCTB or with 50 μg of the appropriate immunogen genetically or chemically linked to rCTB (see group definition) in the presence or absence of an adjuvant amount (1 μg) of CT. Data are from samples obtained two weeks after the last immunization and represent geometric means±SD.

Figure 21:
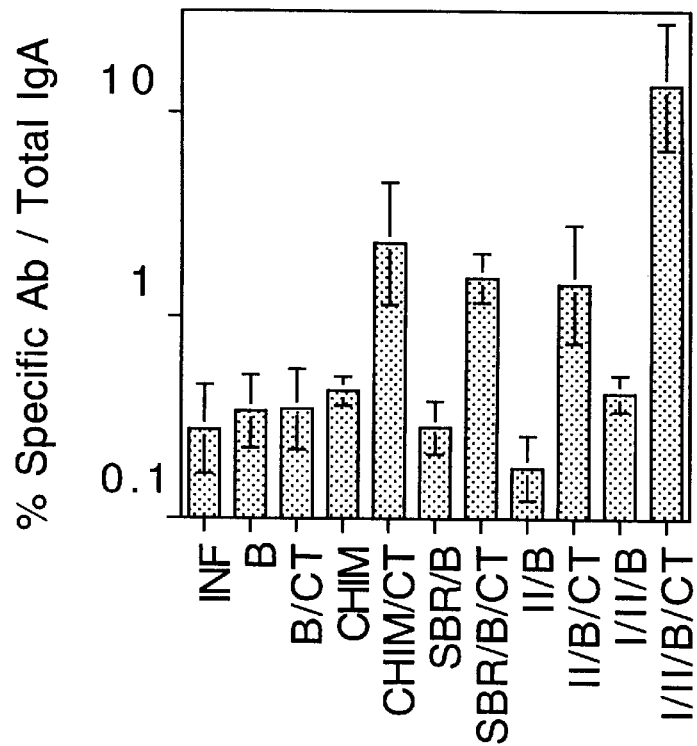

FIG. 21 shows the salivary IgA antibody responses to native AgI/II in intranasally immunized rats. The animals were immunized three times at 14-day intervals with 25 μg of recombinant B subunit of cholera toxin (rCTB) or with 50 μg of the appropriate immunogen genetically or chemically linked to rCTB (see group definition) in the presence or absence of an adjuvant amount (1 μg) of cholera toxin (CT). Data are samples obtained two weeks after the last immunization and represent geometric means±SD.

Figure 22:
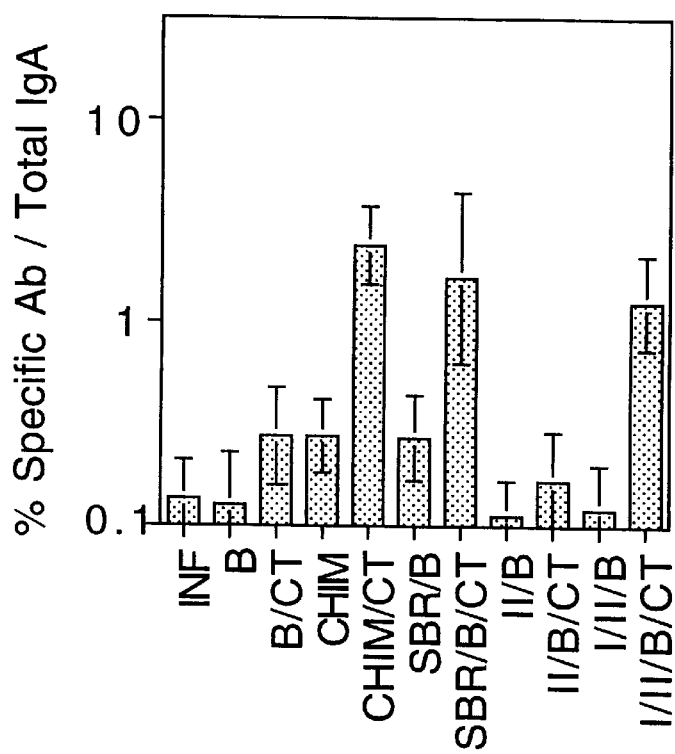

FIG. 22 shows the salivary IgA antibody responses to recombinant SBR (42-kDa saliva-binding region at the N-terminal of AgI/II) in intranasally immunized rats. The animals were immunized three times at 14-day intervals with 25 μg of rCTB or with 50 μg of the appropriate immunogen genetically or chemically linked to rCTB (see group definition) in the presence or absence of an adjuvant amount (1 μg) of CT. Data are samples obtained two weeks after the last immmunization and represent geometric means±SD.

Figure 23:
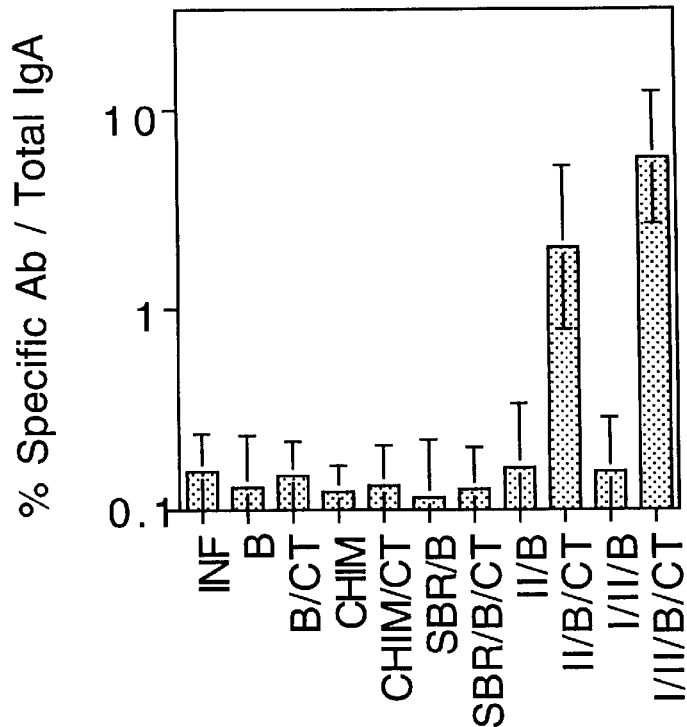

FIG. 23 shows the salivary IgA antibody responses to AgII (C-terminal one-third of AgI/II) in intranasally immunized rats. The animals were immunized three times at 14-day intervals with 25 μg of rCTB or with 50 μg of the appropriate immunogen genetically or chemically linked to rCTB (see group definition) in the presence or absence of an adjuvant amount (1 μg) of CT. Data are from samples obtained two weeks after the last immunization and represent geometric means±SD.

Figure 24:
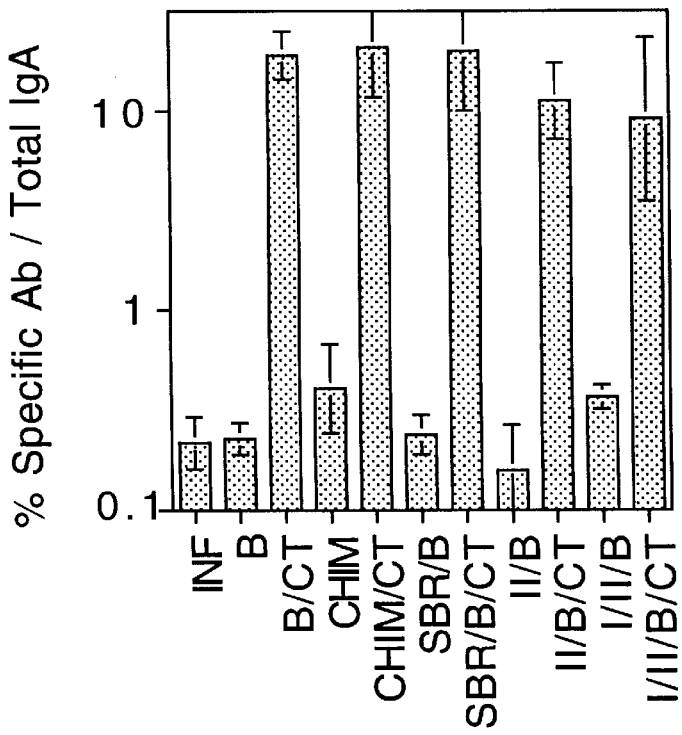

FIG. 24 shows the salivary IgA antibody responses to CT in intranasally immunized rats. The animals were immunized three times at 14-day intervals with 25 μg of rCTB or with 50 μg of the appropriate immunogen genetically or chemically linked to rCTB (see group definition) in the presence or absence of an adjuvant amount (1 μg) of CT. Data are from samples obtained two weeks after the last immunization and represent geometric means±SD.

| Group Abbreviations | Groups Defined |
| --- | --- |
| INF | Unimmunized controls |
| B | rCTB |
| B/CT | rCTB + CT |
| CHIM | SBR-CT$^{ΔA1}$ |
| CHIM/CT | SBWCT$^{ΔA1}$ + CT |
| SBR/B | SBR-rCTB |
| SBR/B/CT | SBR-rCTB + CT |
| II/B | AgII-rCTB |
| II/B/CT | AgII-rCTB + CT |
| I/II/B | AgI/II-rCTB |
| I/II/B/CT | AgI/II-rCTB + CT |

DETAILED DESCRIPTION OF THE INVENTION

The following abbreviations may be used herein: GALT: gut-associated lymphoid tissue; CT: cholera toxin; CTA2/B: cholera toxin subunits A2/B; CTB: cholera toxin subunit B; rCTB:recombinant CTB; i.n.: intranasal; i.g.: intragastric.

As used herein, the term "fusion protein" refers to a single contiguous protein produced by the expression of DNA sequences for one protein fused to DNA sequences encoding a different protein.

As used herein, the term "chimeric protein" refers to a fusion protein assembled with a different protein.

The present invention is directed to a composition of matter comprising a novel plasmid for use as a mucosal immunogen to prevent or inhibit the formation of dental caries. This recombinant plasmid expresses a chimeric protein which is a primary immunogen that induces long term antibody responses. Production of the chimeric protein is optimal at physiological temperatures, i.e., 37° C.

In one embodiment of the present invention, the chimeric protein immunogen is constructed by fusing a large segment of a protein antigen, e.g., Salivary Binding Protein (SBR) from *Streptococcus mutans* surface protein (AgI/II) to the A2 subunit of cholera toxin, and assembling this with cholera toxin B subunits to form the chimeric protein. This is designated SBR-CTA2/B, or SBR-CT$^{ΔA1}$. The latter designation refers to the deletion the A1 subunit of cholera toxin (which is the actual toxic component) from the genetic construct, and its replacement by SBR. "SBR-CTA2/B" is a shorthand molecular formula for the chimeric protein.

Initially, SBR-CTA2/B was produced in *Escherichia coli*, and the purified chimeric protein, was immunogenic by oral or intranasal administration with the generation of serum and salivary antibodies which can last for up to at least 11 months in mice. The duration of antibody responses is novel, and not predictable or expected. The establishment of regulatory T cells is in part intended to build a case for the generation of long-term memory within the mucosal immune system, because that is not 'expected' insofar as is widely held that memory is limited in the mucosal immune system. The chimeric protein of the present invention, when expressed in attenuated *Salmonella typhimurium* produces significant increases in serum IgG and salivary IgA antibody levels after oral immunization.

A second embodiment of the present invention is the expression of SBR-CTA2/B in *Salmonella typhimurium* for delivery in a live carrier (attenuated) organism. The advantages of this construct are that there is no need to purify the product, and that a slightly different spectrum of immune responses may be obtained, with beneficial applications in some diseases.

In another embodiment of the present invention, the recombinant plasmid contains a salivary binding protein-cholera toxin A2/B chimeric protein expressed in *E. coli*. Intragastric immunization of salivary binding protein coupled to CTB in this chimeric protein form leads to increased antigen responsive T cells.

In another embodiment of the present invention, the recombinant plasmid contains a salivary binding protein-cholera toxin$^{AA1}$ chimeric protein expressed in *Salmonella typhimurium*. Oral immunization using this recombinant plasmid results in increased serum IgG responses to antigen. Oral immunization using this recombinant plasmid also resulted in increased salivary IgA antibody responses to antigen.

There are many potential uses for the technology of the present invention in mucosal vaccine development. The basic method is amenable to almost any other protein antigen that can be cloned and inserted into the construct instead of SBR. For example, a protein antigen from *Streptococcus pneumoniae* can be used to make a potential vaccine against pneumonia. Similarly, constructs from group A streptococcal proteins or a vaccine against *Helicobacter pylori* can be prepared using the methodology disclosed in the instant specification. Various applications of the present invention can be incorporated into commercial products, i.e., vaccines for the generation of immune responses that would afford protection against infections, or various modifications of the immune response. These are based on the use of CTA2/B chimeric proteins that include protein segments from a variety of microorganisms, intended for administration orally or intranasally, or possibly by other mucosal routes (e.g., rectally or intra-vaginally).

For example, one may prepare vaccines to generate immunity to the organisms responsible for dental caries, i.e., the "*mutans*" streptococci (*Streptococcus mutans* and *Streptococcus sobrinus*). This is based on the saliva-binding region of *S. mutans* AgI/II, as described above. Secondly, one may prepare vaccines against *Streptococcus pyogenes* ("strep. throat and its sequelae including acute rheumatic fever and acute glomerulonephritis, scarlatina, streptococcal toxic shock, and other infections). Further, one may prepare: vaccines against *Streptococcus pneumoniae* (pneumococcal pneumonia, otitis media, meningitis) using sequences from pneumocoal surface proten A (PspA), vaccines against: a) *neisseria meningitidis* (meningococcal meningitis, otitis media) using neisserial surface protein A (NspA-men); b) *Neisseria gonorrhoeae* (gonorrhea) using neisserial surface protein A (NspA-gon); c) *Streptococcus pneumoniae* (pneumococcal pneumonia, otitis media, meningitis) using other pneumococcal protein antigen; d) vaccines against *Streptococcus equi* ("strangles" in horses) using a *Streptococcus equi* surface protein; e) vaccines against influenza virus *helicobacter pylori* (gastric ulcer), respiratory pathogens including *Pseudomonas aeruginosa*, f) contraceptive vaccines using zona pellucida antigens; g) vaccine against respiratory syncytial virus; h) generation of "oral tolerance" to auto-antigens (auto-immune conditions); i) vaccines against mycoplasma infections; and j) vaccines against *Staphylococcus aureus* protein A.

In yet another embodiment, the vaccine construction technology of the present invention can be used to generate immunity mediated by so-called cytotoxic T cells instead of antibodies. This methodology would have applications especially against viral infections.

Thus, the present invention is directed to a plasmid capable of replication in a host which comprises, in operable linkage:

a) an origin of replication; b) a promoter; and c) DNA sequences encoding the A2 subunit of cholera toxin. In addition, the plasmid may further comprise DNA sequences encoding subunit B of cholera toxin fused to the A2 subunit of cholera toxin. One such preferred plasmid is pCT$^{AA1}$ (deposited with ATCC, 10801 University Blvd., Manassas, Va. 20110-2209 on May 4, 1999, designation PTA-4). In another embodiment, the plasmid further comprises salivary binding protein (SBR) from *Streptococcus mutans* surface protein (AgI/II) fused to the A2 subunit of cholera toxin. One such preferred plasmid is designated pSBR-CTA2/B or pSBR-CT$^{AA1}$ (deposited with ATCC, 10801 University Blvd., Manassas, Va. 20110-2209 on May 4, 1999, designation PTA-5).

In another embodiment, the present invention is directed to a plasmid capable of replication in a host which comprises, in operable linkage: a) an origin of replication; b) a promoter; and c) DNA sequences encoding the A2 subunit of cholera toxin, further comprising DNA sequences encoding an antigen of interest fused to DNA sequences encoding the A2 subunit of cholera toxin. In addition, there is provided a capable of replication in a host which comprises, in operable linkage: a) an origin of replication; b) a promoter; and c) DNA sequences encoding the A2 subunit of cholera toxin further comprising DNA sequences encoding an antigen of interest fused to DNA sequences encoding the A2 subunit of cholera toxin. This plasmid may further comprises salivary binding protein (SBR) from *Streptococcus mutans* surface protein (AgI/II) fused to the A2 subunit of cholera toxin. The present invention also relates to chimeric proteins and fusion proteins produced by the plasmids of the present invention.

In another embodiment, the present invention is directed to an attenuated bacterial strain containing a plasmid of the present invention. In a preferred embodiment, the bacterial strain is Salmonella.

In another embodiment, the present invention is directed to a method of producing an immune response to a protein antigen of interest in an individual in need of such treatment, comprising the step of administereing to said individual a pharmacologically effective dose of a chimeric protein of the present invention. The protein may be administered by a route selected from the group consisting of orally, intranasally, intrarectally, intravaginally, intramuscularly, and subcutaneously. Preferably, the immune response results in the production of antibodies to the protein antigen sequence in a bodily fluid selected from the group consisting of saliva, intestinal secretions, respiratory secretions, genital secretions, tears, milk and blood. Preferably, the immune response is selected from the group consisting of development of antigen-specific T cells in the circulation and tissues of said individual, the development of cytotoxic T cells and immunological tolerance to the protein antigen sequence.

The following examples are given for the purpose of illustrating various embodiments of the invention and are not meant to limit the present invention in any fashion.

EXAMPLE 1

One object of the present invention was to demonstrate the duration of antibody responses to the AgI/II adhesin after oral immunization of mice with SBR-CT$^{\Delta A1}$ about 1 year earlier. One group consisted of five mice previously given three doses of 100 μg of SBR-CT$^{\Delta A1}$ together with 5 μg of intact CT as an adjuvant (except for animal #5 in FIGS. 1A/1C and FIGS. 2A/2C, the mice were given the dose adsorbed on Al(OH)$_3$, which was shown to enhance serum IgG antibody responses after oral immunization).

A second group comprised three similarly treated mice with the exception that they were immunized in the absence of intact CT. A third group consisting of six mice which were sham immunized with buffer only were used as naive controls. Saliva and serum samples were collected 11 months after the last dose of the primary immunization and all three groups of mice were subsequently given 100 μg of SBR-CT$^{\Delta A1}$ by gastric intubation. CT adjuvant (5 μg) was co-administered to those mice that had also received CT during the primary immunization, and to half of the naive control animals. Samples of saliva and serum were collected again 7 days after the booster immunization and antibody responses were evaluated by ELISA on plates coated with native AgI/II and CT. Unknown antibody concentrations were calibrated against mouse immunoglobulin reference serum standards assayed simultaneously in the same microtiter plate. Results were evaluated by Student's t test using the MultiStat program (Biosoft, Cambridge, UK) with a Macintosh computer. Differences were considered significant at the $P<0.05$ level.

Figure 1A:
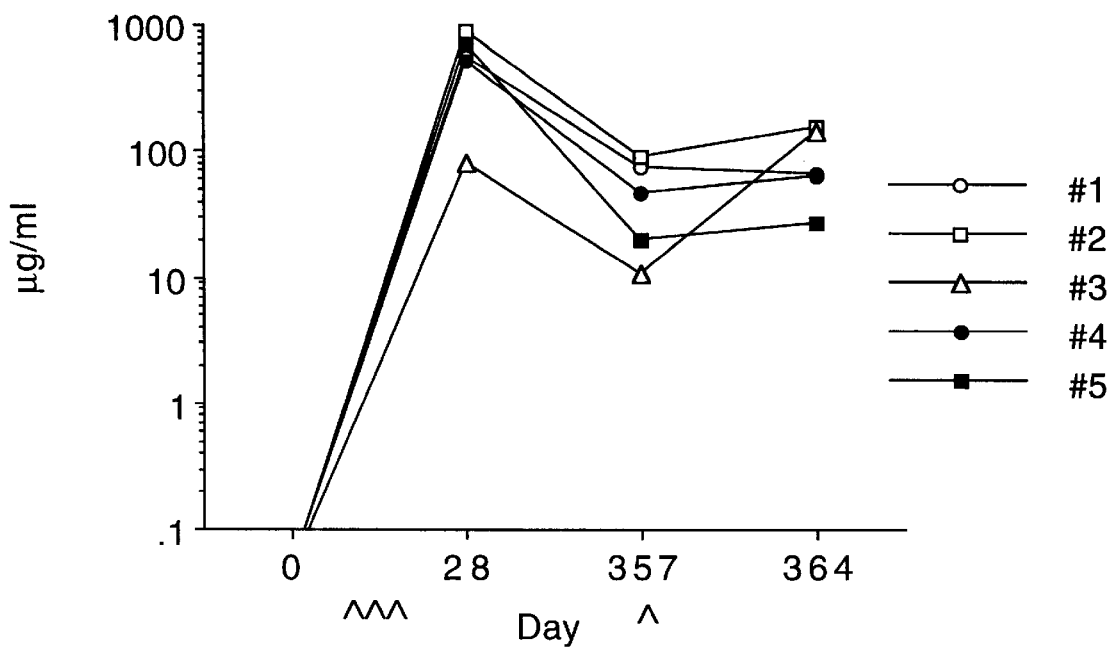
FIGS. 1(A)–1(D) shows the persistence of serum IgG antibody to AgI/II and CT after peroral immunization of mice with SBR-CT$^{\Delta\Delta1}$ chimeric protein ($^{\wedge\wedge\wedge}$) and a single booster immunization 11 months later ($^{\wedge}$). Mice were given the immunogen in the presence (FIG. 1A and FIG. 1C) or absence FIG. 1B and FIG. 1D of CT adjuvant. Data are presented for each mouse individually.
Figure 1B:
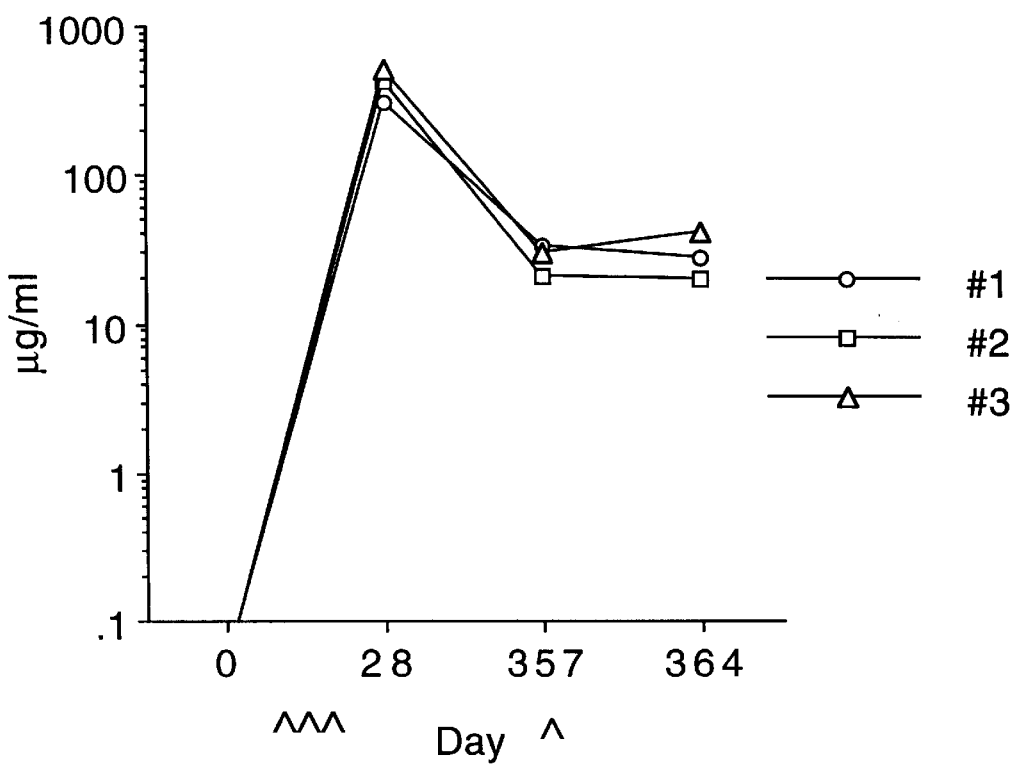
Figure 1C:
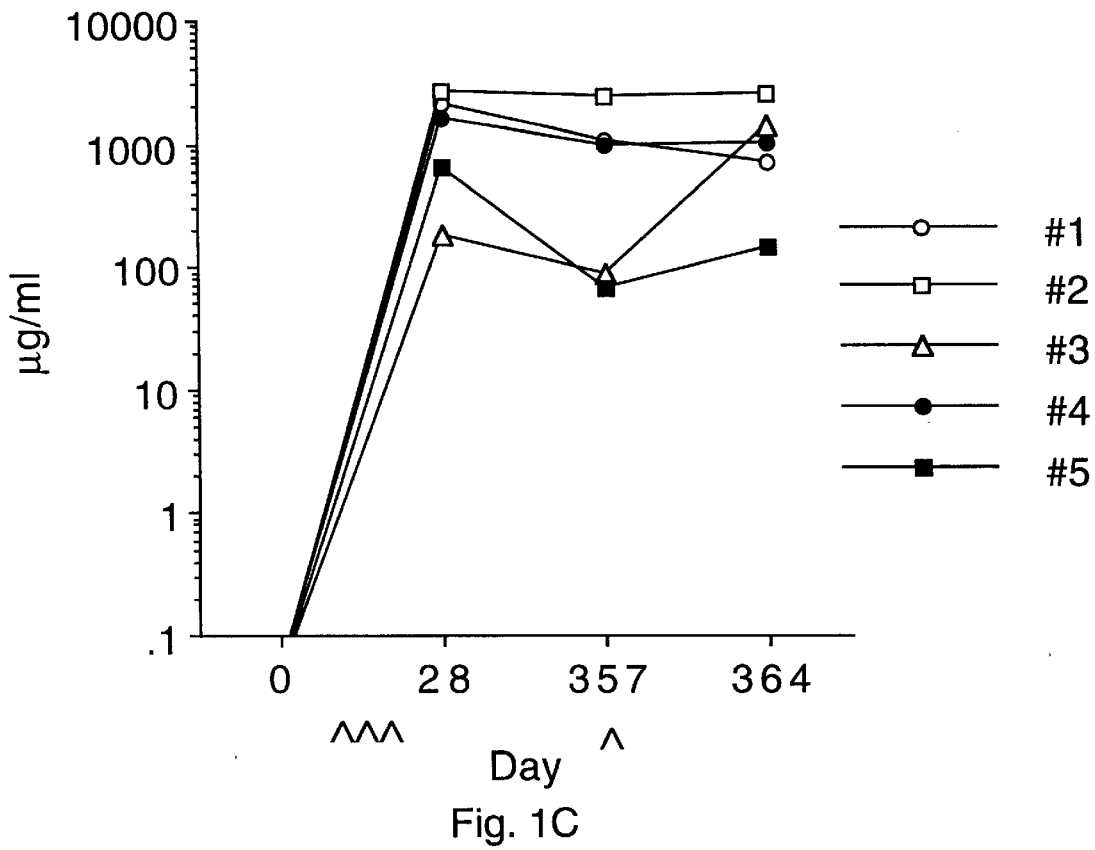
Figure 1D:
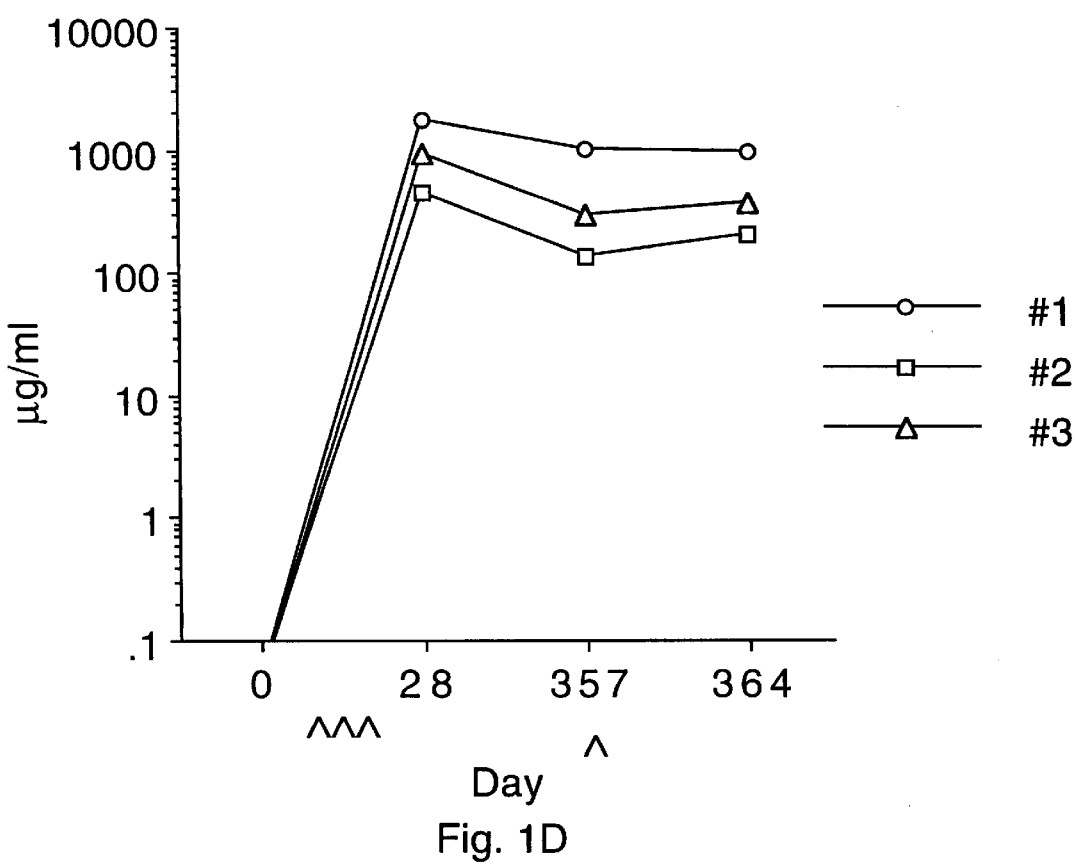
Figure 2A:
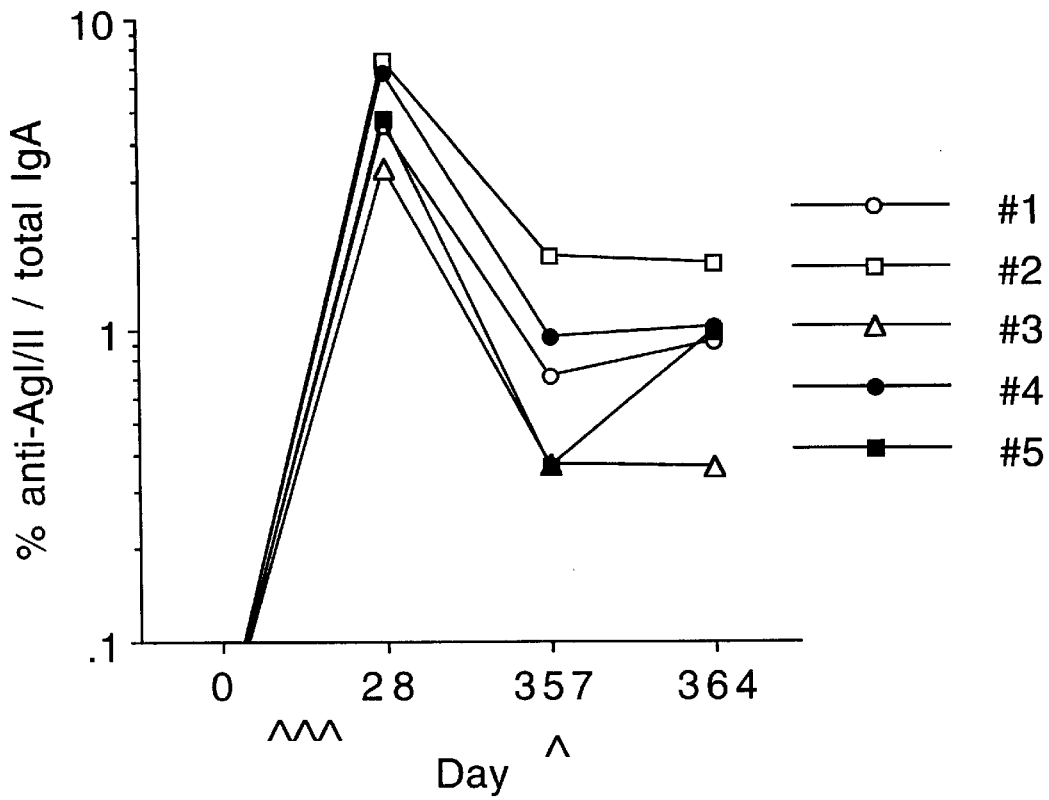
FIGS. 2(A)–2(D) shows the duration of salivary IgA antibody to AgI/II and CT following peroral immunization of mice with SBR-CT$^{\Delta\Delta1}$ chimeric protein ($^{\wedge\wedge\wedge}$) and a single booster immunization 11 months later ($^{\wedge}$). Mice were given the immunogen in the presence FIG. 2A and FIG. 2C or absence FIG. 2B and FIG. 2D of CT adjuvant. Data are presented for each mouse individually.
Figure 2B:
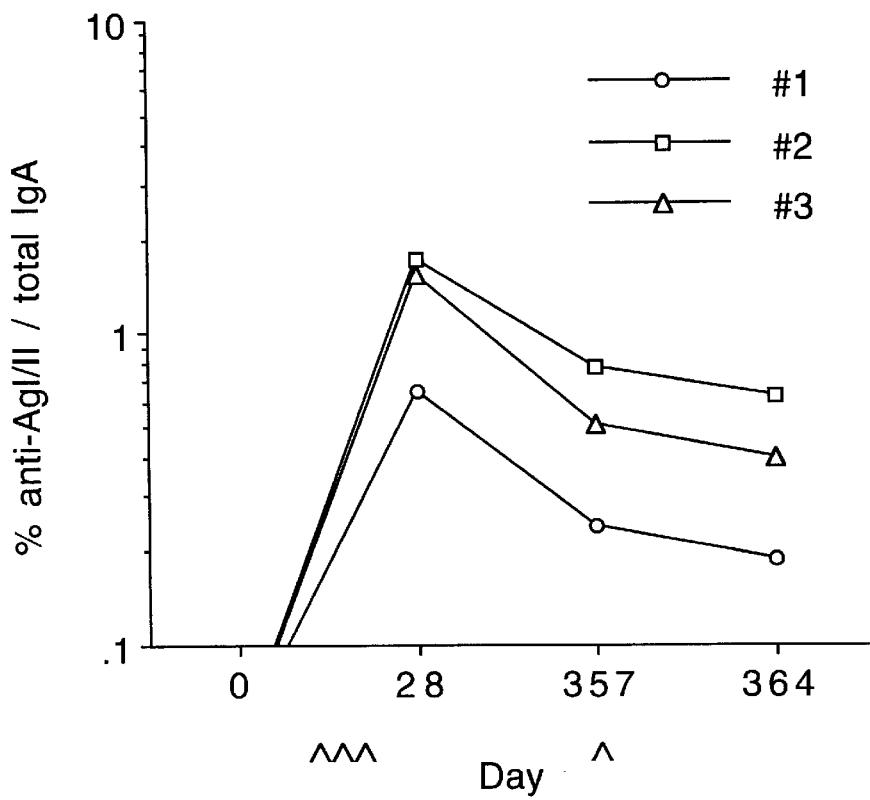
Figure 2C:
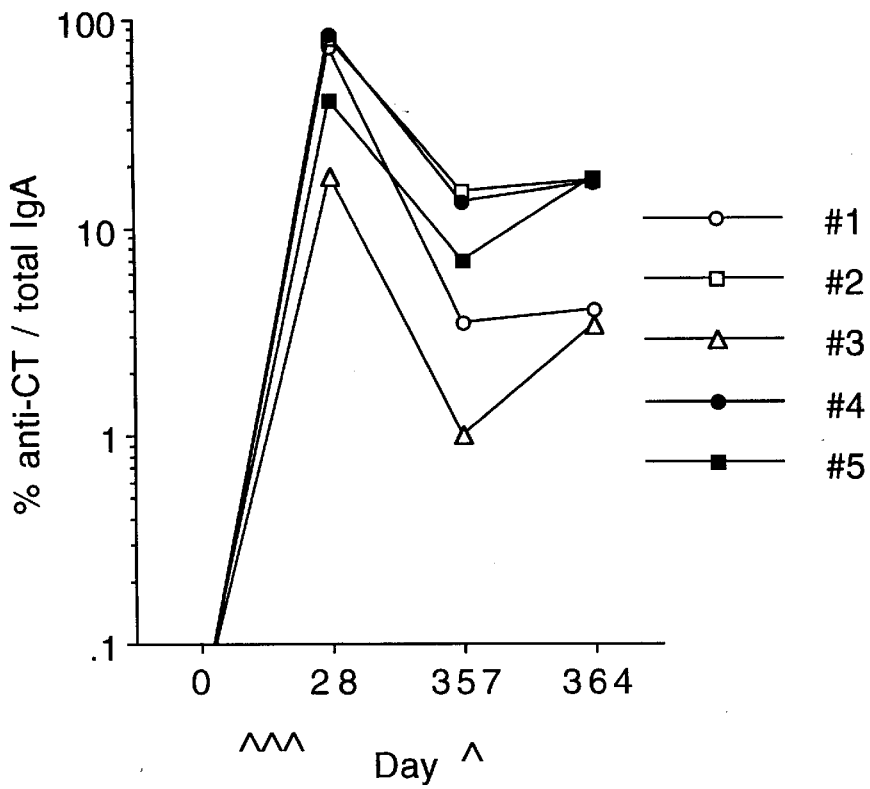
Figure 2D:
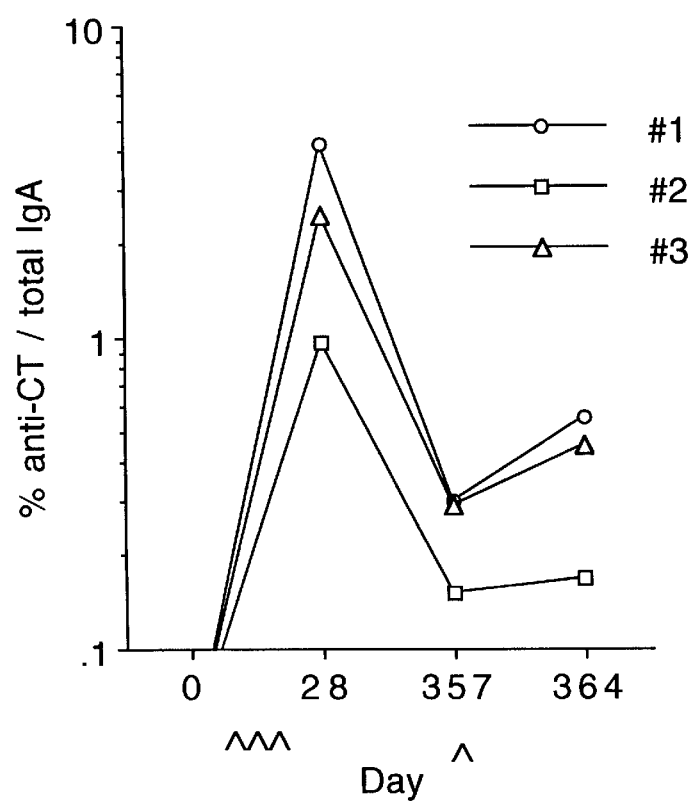

Substantial levels of serum IgG (FIGS. 1A and 1B) and salivary IgA (FIGS. 2A and 2B) antibodies to AgI/II and CT persisted at least until day 357, although lower than immediately after immunization (day 28), even in mice that did not receive an adjuvant dose of intact CT (FIGS. 1B and 1D plus FIGS. 2B and 2D). During the same period, the six sham-immunized mice did not develop detectable serum or salivary antibody responses, except two animals that showed trace levels of salivary IgA to AgI/II (0.15 and 0.12 % antibody/total IgA). However, the response of the sham-immunized group (0.05±0.07% antibody/total IgA) was significantly less ($P<0.05$) than the salivary responses in either of the immunized groups (0.82±0.56% antibody/total IgA (FIG. 2A) and 0.51±0.27% antibody/total IgA (FIG. 2B)). The prolonged duration of antibody responses might be explained by persisting antigen providing continuous low-level stimulation of memory cells. The mechanism of antigen persistence may involve follicular dendritic cells which bind antigen-antibody complexes via cell surface Fc receptors and slowly release them over long periods. Alternatively, the existence of molecules cross-reacting with AgI/II (or cross-reactive enterotoxins in the case of CT) cannot be ruled out, although S. mutans is not a natural inhabitant of the murine oral cavity.

A recall response was not observed in serum after the oral booster immunization (FIGS. 1A and 1C), as the antibody responses to AgI/II and CT before and immediately after the booster immunization were not significantly different. However one mouse (#3 in FIG. 1C) that had the lowest antibody levels to CT showed a remarkable 16-fold increase resulting in a higher final response than was observed shortly after the primary immunization. This mouse also showed an enhanced anamnestic IgG response to AgI/II which was 13 times higher than observed immediately prior to the boost (FIG. 1A). This finding suggests that anamnestic responses are not readily elicited in the presence of a relatively high persisting antibody response. As expected, naive mice developed a poor IgG antibody response to AgI/II or CT upon challenge with one dose of SBR-CT$^{\Delta A1}$.

An enhanced salivary IgA anamnestic response was not observed in these mice following the oral booster immunization, even when CT was used as an adjuvant (FIGS. 2A and 2C). Trace levels of salivary antibody to AgI/II observed in two of the six naive mice were not altered after the single booster immunization, while the remaining mice did not develop any salivary response. It appears that, after peroral immunization, the anamnestic response in the salivary glands may depend on recruitment of memory cells from the Peyer's patches or other mucosal induction sites, whereas the gut lamina propria may possess an additional source of memory represented by local memory cells that differentiate into plasma cells upon in situ activation by antigen adsorbed through intestinal epithelial cells. This might result in the memory response being manifested more readily at the gut lamina propria than at a remote effector site such as the salivary glands.

SBR represents an AgI/II adherence domain that mediates the binding of S. mutans to the saliva-coated tooth surfaces. S-IgA antibodies to the whole AgI/II molecule inhibit S. mutans adherence in vitro as well as S. mutans colonization and dental caries development in vivo. Since S. mutans infects more than 95% of the human population and caries is a common infectious disease, the continuous presence of salivary S-IgA as well as serum-derived IgG antibodies may be necessary to suppress an organism that is continually present in the oral cavity. The present invention shows that induction of long-term antibody responses is possible upon primary immunization with the SBR-CT$^{\Delta A1}$ chimeric protein. This is further supported by the finding that AgI/II-responsive T cells persist in cervical and mesenteric lymph nodes for now up to eleven months after immunization. This immunization strategy applied to other mucosal infections by linking candidate immunogens to CT$^{\Delta A1}$, may similarly elicit prolonged mucosal antibody responses.

EXAMPLE 2

Strain Construction

SBR-CT$^{\Delta A1}$ was expressed in S. typhimurium BRD509, an aroA$^-$ aroD$^-$ oral vaccine strain after electrotransformation with plasmids pSBR-CT$^{\Delta A1}$ and pGP-1-2 using a gene pulser (Biorad, Richmond, Calif.) set at 2.5 kV, 25 μF, and 200 Ohms. The for mer plasmid expresses SBR-CT$^{\Delta A1}$ under the inducible control of the bacteriophage T7 promoter, while the latter provides a source of T7 RNA polymerase that is temperature-regulated. Specifically, the T7 RNA polymerase is under the control of the 1 $P_L$ promoter that is regulated by the cI857 temperature-sensitive 1 repressor. Colonies transformed with both plasmids were selected on L-agar plates (1% tryptone, 0.5% yeast extract, 0.5% NaCl, 0.1% dextrose, 1.5% agar) supplemented with 50 μg/ml carbenicillin plus 50 μg/ml kanamycin (to select for pSBR-CT$^{\Delta A1}$ and pGP1-2, respectively). Transformants were examined for the presence of plasmids with sizes of 5.6 and 7.2 kilobases, corresponding to the size of pSBR-CT$^{\Delta A1}$ and pGP1-2, respectively.

EXAMPLE 3

Target Protein Expression and Localization

Colonies positive for both pGP1-2 and pSBR-CT$^{\Delta A1}$ were grown at 30° C. in L-broth containing the appropriate antibiotics and target gene expression was induced at mid-log phase by a temperature shift to 42° C. After 30 minutes the cultures were returned to 30° C. and incubation was continued for an additional 90 minutes. To determine expression of SBR-CT$^{AA1}$, whole-cell lysates were examined by $G_{M1}$-ELISA for the presence of a $G_{M1}$ ganglioside-binding soluble protein that would react with polyclonal antibodies to CTB or AgI/II, or with a monoclonal antibody specific for the SBR of AgI/II. The insoluble pellet was then processed and possible inclusion bodies were isolated, solubilized by boiling in sodium dodecyl sulfate (SDS) buffer (the amount used was proportional to the final absorbance at 600 nm of the corresponding cultures), and samples (3 μl) analyzed by SDS-polyacrylamide gel electrophoresis (SDS-PAGE) on 12.5% gel. To determine whether SBR-CT$^{AA1}$ is transported to the periplasm, periplasmic extracts were prepared by either the spheroplast formation method or by cold osmotic shock. The extracts obtained were essentially free of cytoplasmic contamination ($\leq 2\%$) as determined by assaying the activity of glucose-6-phosphate dehydrogenase, a cytoplasmic marker enzyme. The total protein content of the extracts was estimated by the bicinchoninic acid protein assay method (Pierce, Rockford, Ill.) using bovine serum albumin as the standard.

EXAMPLE 4
Oral Immunization

The bacteria were grown at 30° C. to an optical density at 600 nm of 0.5–0.6, harvested by centrifugation, and resuspended in a medium consisting of 4 parts Hank's balanced salt solution (Life Technologies Inc., Grand Island, N.Y.) and 1 part sodium bicarbonate (7.5% solution; Mediatech, Washington, D.C.). The number of bacteria in the suspension was estimated by extrapolating from a growth curve and was confirmed by plating dilutions on L-agar plates (with or without the appropriate antibiotics) and enumerating the colonies grown after overnight incubation at 30° C. The immunizing dose ($10^9$ colony-forming units in 0.25 ml) was administered to 10-week old BALB/c mice by intragastric intubation using a 22-gauge feeding tube (Popper and Sons Inc., Hyde Park, N.Y.). The animals were immunized on days 0 and 49 and sampled at weekly or bi-weekly intervals. Serum was obtained from tail vein blood samples and saliva was collected after stimulation of the salivary flow by intraperitoneal injection of 5 μg carbachol. Serum IgG and salivary IgA antibodies were determined by ELISA on microtiter plates coated with AgI/II or $G_{M1}$ ganglioside followed by CT, while total salivary IgA concentrations were assayed on plates coated with antibodies to mouse IgA. Peroxidase-conjugated antibodies to mouse IgG or IgA were used as detection reagents (Southern Biotechnology Associates, Birmingham, Ala.). The amount of antibody/immunoglobulin in test samples was calculated by interpolation on standard curves generated using a mouse immunoglobulin reference serum and constructed by a computer program based on four parameter logistic algorithms (Softmax, Molecular Devices, Menlo Park, Calif.). Results were evaluated by Student's t test and differences were considered significant at the $P<0.05$ level.

EXAMPLE 5
Results

Recombinant *S. typhimurium* BRD509 positive for both pGP1-2 and pSBR-CT$^{AA1}$ was shown to produce a protein that bound the $G_{M1}$-ganglioside receptor and possessed CTB and AgI/II epitopes, in contrast to the original BRD509 strain or clones containing either pGP1-2 or pSBR-CT$^{AA1}$ alone (TABLE I). Since the pSBR-CT$^{AA1}$ encodes for the signal peptides of CTB and SBR-CTA2, it was of interest to determine whether the chimeric protein was transported into the periplasm where assembly of its components takes place.

TABLE I $G_{M1}$ Ganglioside-binding activity and antigenicity of soluble protein extracts[a] from recombinant *S. typhimurium* BRD509 clones

| Plasmid | ELISA value[b] of clone extract developed with | | |
|---|---|---|---|
| | Anti-CTB | Anti-AgI/II | Anti-SBR |
| None | 0.017 | 0.003 | 0.001 |
| pGP1-2 | 0.009 | 0.017 | 0.008 |
| pSBR-CT$^{AA1}$ | 0.02 | 0.013 | 0.004 |
| pGP-1-2 + pSBRCT$^{AA1}$ | 2.052 | 1.005 | 1.01 | a = assayed at 20 μg total protein/ml; b = mean optical density at 490 nm

To examine this, a calibrated $G_{M1}$-ELISA standardized with purified SBR-CT$^{AA1}$ was used to detect and quantify the chimeric protein in periplasmic and in whole-cell extracts under uninduced and induced (temperature shift from 30° C. to 37° C. or 42° C. for 30 minute) conditions. As shown in TABLE II, SBR-CT$^{AA1}$ was found in the periplasm of *S. typhimurium* BRD509 (pGP1-2+pSBR-CT$^{AA1}$) and of *E. coli* BL21(DE3) (pSBR-CT$^{AA1}$) which contains a chromosomal copy of the T7 RNA polymerase gene under the control of the lacUV5 promoter. The chimeric protein was not detected in the periplasm or whole-cell lysates of a negative control clone lacking pSBR-CT$^{AA1}$ (TABLE II). Although cellular location of the foreign antigen may affect the immune response, secretion of a protein into the periplasm may enhance its stability by preventing degradation.

TABLE II

Localization of SBR-CT$^{AA1}$ Chimeric Protein in the Periplasmic Space

Figure 3:
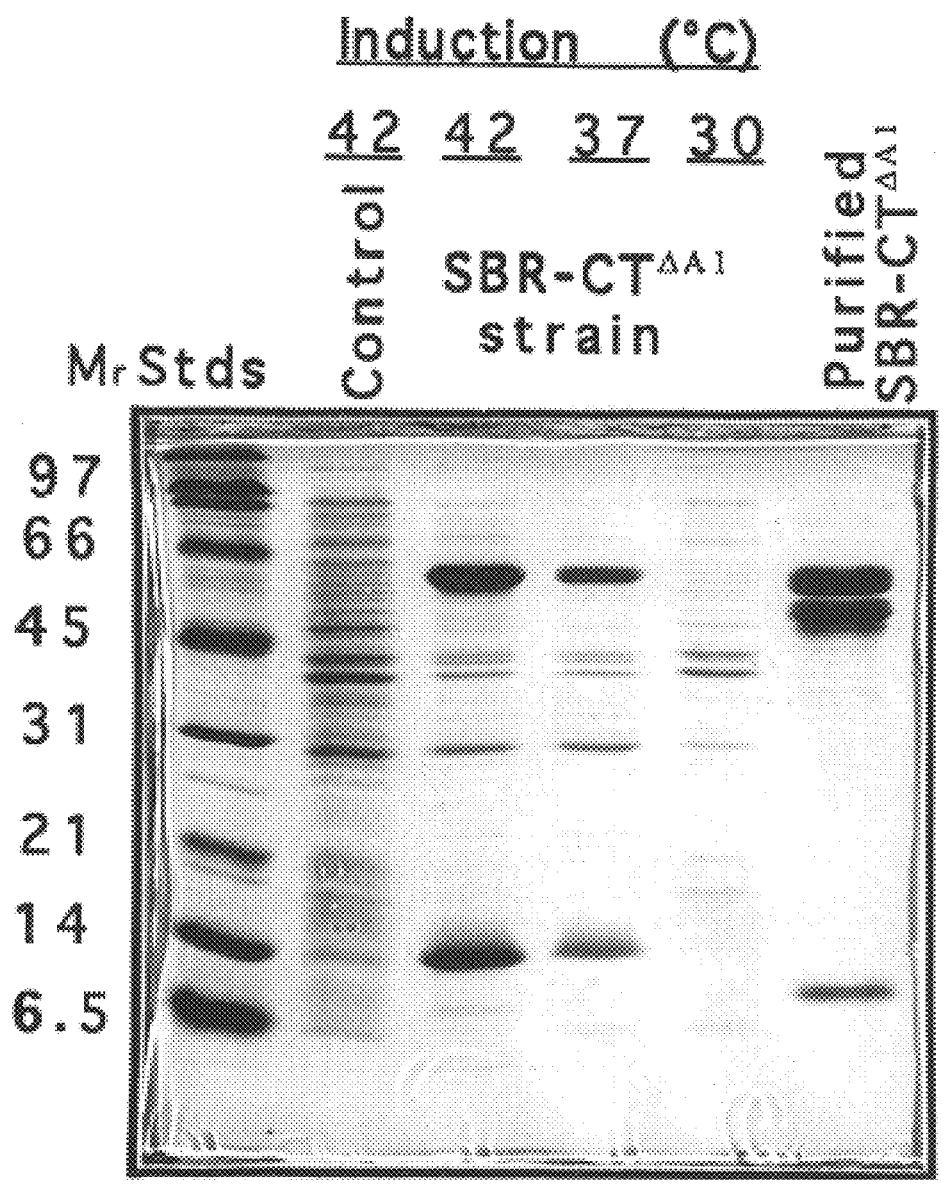
FIG. 3 shows the SDS-PAGE analysis of inclusion bodies produced under different induction conditions by *S. typhimurium* expressing the SBR-CT$^{\Delta\Delta1}$ chimeric protein. A related strain lacking SBR-CT$^{\Delta\Delta1}$ was used as a negative control. Two prominent bands migrating at about 60 kDa and about 14 kDa present in the expressing strain after 42° C. induction (and to a lesser extent after 37° C. induction)

| Strain | Induction | Periplasmic fraction obtained by: | | Whole Cell lysate |
|---|---|---|---|---|
| | | Spheroplast formation | Osmotic Shock | |
| *E. coli* BL21 (DE3) (pSBR-CT$^{AA1}$) | IPTG[a] | 271[b] | 319 | 99.7 |
| S. typ. BRD509 (pGP1-2) | 42° C. | 0 | 0 | 0 |
| S. typ. BRD509 (pGP1-2 + PSBR-CT$^{AA1}$) | None | 77.3 | 98.5 | 20.2 |
| S. typ. BRD509 (pGP1-2 + pSBR-CT$^{AA1}$) | 37° C. | 239 | 314 | 119 |
| S. typ. BRD509 (pGP1-2 + pSBR-CT$^{AA1}$) | 42° C. | 119 | 123 | 53.6 | a = isopropyl-β-D-thiogalactoside
b = μg SBR-CT$^{AA1}$/mg protein in the extracts Under uninduced conditions, the chimeric protein was produced at about 20 μg per mg of total soluble protein (TABLE II) or 7–9 μg per $10^9$ bacteria. This finding is likely due to residual expression of the T7 RNA polymerase. Indeed, the temperature-sensitive 1 repressor on pGP1-2 does not tightly repress the 1 $P_L$ promoter which consequently allows low-level production of the polymerase at 30° C. The amount of soluble chimeric protein increased several-fold following induction at 37° C., whereas at 42° C. the increase was minimal (TABLE II) with concomitant accumulation of SBR-CT$^{AA1}$ in inclusion bodies (FIG. 3). This suggests that at physiological body temperature (36–37° C.) production of soluble chimeric protein may be optimal.

Recombinant *S. typhimurium* expressing SBR-CT$^{AA1}$ was routinely grown under uninduced conditions (30° C.) at which it showed optimal growth. Although the SBR-CT$^{\Delta A1}$-expressing *S. typhimurium* strain does not possess a temperature-sensitive mutation, temperatures higher than 30° C. cause gradual induction of the highly-efficient T7 RNA polymerase which may interfere with gene transcription by the host RNA polymerase. Additionally overexpression of the cloned chimeric protein at 37° C. could interfere with bacterial growth. The strain was also found to be immunogenic since oral administration of $10^9$ bacteria in mice resulted in serum IgG and salivary IgA antibody responses to Salmonella and native AgI/II and CT (FIGS. 4A and 4B). An oral booster immunization 7 weeks later significantly enhanced the serum IgG response to AgI/II and CT ($P<0.05$) but not to Salmonella, the response to which reached high levels even before the secondary immunization (FIG. 4A). Salivary IgA antibodies to Salmonella and the cloned antigens were detected 3 weeks after the primary immunization (FIG. 4B). The salivary response to AgI/II approached the level of 1% specific IgA antibody/total IgA but was not enhanced after the booster immunization. This is in contrast to the response against CT or Salmonella, where the increase in the response to CT or Salmonella reached statistical significance at weeks 8 or 10, respectively.

The salivary IgA response to AgI/II (≈1% antibody/total IgA) after a single oral immunization with Salmonella is similar to that observed after 3 doses of 100 μg purified SBR-CT$^{\Delta A1}$ in the absence of intact CT adjuvant. The immunizing dose ($10^9$ bacteria) was estimated to contain 7–9 μg of chimeric protein, but this probably does not reflect the amount of SBR-CT$^{\Delta A1}$ delivered in vivo, which would largely depend on the extent of tissue colonization by Salmonella.

In the present invention, the SBR-CT$^{\Delta A1}$ chimeric protein was expressed in attenuated *S. typhimurium* and oral immunization with this recombinant strain resulted in serum IgG and salivary IgA antibody responses against Salmonella and the cloned antigens. Since the SBR segment of AgI/II plays an important role in *S. mutans* colonization, salivary IgA antibodies to SBR may confer protection against this oral pathogen.

EXAMPLE 6

Antigens

AgI/II was purified chromatographically from the culture supernatant of *S. mutans* essentially as described by Russell, et al., 1980, 28:486–493. The SBR-CTA2/B chimeric protein was constructed and expressed in *E. coli* and purified from extracts. In essence, this consisted of PCR-amplifying DNA for a 42-kDa segment encompassing the A-repeat region and some downstream sequence of AgI/II from the pac gene, ligating this in a modified pET20b(+) plasmid (Novagen, Inc., Madison Wis.) in frame with and upstream of the genes for CTA2 and CTB, and transforming the recombinant plasmid into *E. coli* BL21(DE3) cells (Novagen).

SBR polypeptide was obtained by excising the relevant DNA and religating it into unmodified pET20b(+) in order to express SBR with a 6-residue histidine sequence derived from the plasmid. This plasmid was also expressed in *E. coli* BL21(DE3), and SBR was purified from cell lysates by metal-chelation chromatography on a nickel-loaded column (Novagen), according to the manufacturer's instructions. CT and CTB were purchased from List Biological Laboratories, Inc. (Campbell Calif.).

EXAMPLE 7

Animals and Immunization

Adult BALB/c mice of either sex, 14 to 20 weeks old, from a pathogen-free colony, were used for all experiments. Groups of 9 mice were immunized i.g. 3 times at 10-day intervals by gastric intubation of either SBR-CTA2/B (100 μg) alone, SBR-CTA2/B together with 5 μg of CT as an adjuvant, or an equimolar amount of SBR (40 μg), all given in 0.5 ml of 0.35M $NaHCO_3$. Serum and saliva samples were collected on day 0 and 10 days after each immunization for assay of antibodies by ELISA. In some experiments, subgroups of 3 mice were killed 10 days after each immunization, for the preparation of cells from PP, MLN, and spleens for T cell proliferation and flow cytometric analyses.

EXAMPLE 8

ELISA

Serum IgG and salivary IgA antibodies to AgI/II, and total salivary IgA concentrations were determined by ELISA, as described by Russell, et al., 1991, *Infect. Immun.* 59:4061–4070, on plates coated with AgI/II or anti-mouse IgA, respectively, and using goat anti-mouse IgG and IgA peroxidase conjugates as detection reagents (Southern Biotechnology Associates, Inc., Birmingham Ala.). Unknowns were interpolated on calibration curves constructed by a computer program based on four parameter logistic algorithms.

EXAMPLE 9

Preparation and Culture of Lymphoid Cells

Single-cell suspensions were obtained by teasing PP, MLN, and spleen apart with needles, and tissue debris was removed by filtering through nylon mesh. Peripheral blood mononuclear cells were obtained by centrifugation on Histopaque 1083 (Sigma Diagnostic, St. Louis, Mo.). Remaining erythrocytes were lysed in buffered ammonium chloride, the cells were washed thrice in RPMI 1640 (Cellgro) medium supplemented with 2% fetal calf serum (FCS), and were finally resuspended 10% FCS/RPMI 1640. Cells were cultured in 10% FCS/RPMI 1640 supplemented with 1 mM sodium pyruvate (Cellgro), non-essential amino acids (Cellgro), 2 mM glutamine (Cellgro), 100 U/ml penicillin-streptomycin (Cellgro), 25 mM HEPES (Sigma), and 0.01 mM 2-mercaptoethanol (Sigma).

EXAMPLE 10

Flow Cytometry

Cell marker expression on freshly isolated cells was determined by double-staining with biotinylated anti-CD4 (GK1.5) followed by avidin-phycoerythrin, and either FITC-conjugated anti-CD3 (145-2C11) or FITC-conjugated anti-CD8 (53-6.72), by incubating for 30 minutes at 4° C. in 2% FCS/Dulbecco's PBS with 0.02% $NaN_3$. Cells were washed, fixed in 1% paraformaldehyde overnight, and analysed on a FACStar IV flow cytometer (Becton-Dickinson).

EXAMPLE 11

Proliferation Assay

Cells from PP, MLN, and spleen were incubated at $10^5$ cells/well (0.1 ml) in triplicate with a previously optimized concentration of AgI/II (0.5 μg/ml) for 5 days, and were pulsed with $^3$[H]-thymidine (0.5 μCi/well) 8 hours before harvesting. Uptake of $^3$[H] was counted by liquid scintillation counter. The stimulation index was calculated as: cpm (wells with AgI/II)/mean cpm (control wells).

EXAMPLE 12

Cytokine Expression

The expression of cytokines by PP, MLN, and spleen cells after culture in vitro with or without AgI/II (0.1 µg/ml) for 24 hours was determined by a reverse-transcription and polymerase chain-reaction (RT-PCR) procedure for the amplification of cytokine mRNA. Cells (5–7×10$^6$) were harvested from the cultures, washed thoroughly, and then lysed in 350 µl of lysing buffer for isolation of RNA using the RNeasy kit (Qiagen Inc., Chatsworth Calif.). RNA was redissolved in 40 µl of diethyl pyrocarbonate-treated water, and 2 µl samples were added to 18 µl of RT mixture (Perkin-Elmer, Foster City Calif.) containing 1× PCR buffer, 5 mM MgCl$_2$, 1 mM of each deoxyribonucleoside triphosphate, 1 U/ml RNase inhibitor, 2.5 U/ml Moloney murine leukemia virus reverse transcriptase, and 2.5 mM Oligo d(T)$_{16}$. Mixtures were overlaid with 50 µl of light mineral oil and incubated in a thermal cycler (Perkin-Elmer) for 15 minutes at 42° C., 45 minutes at 37° C., 5 minutes at 99° C., and 5 minutes at 4° C. After reverse transcription, 80 µl of PCR mixture (Perkin-Elmer) was added to each tube to give final concentrations of 25 U/ml AmpliTaq DNA polymerase, 0.15 µM 5' primer, 0.15 µM 3' primer, 2 mM MgCl$_2$, and 1× PCR buffer II. Primers specific for murine IFN-γ, IL-2, IL-4, IL-5, IL-6, IL-10, and β-actin were obtained from Clontech Laboratories Inc. (Palo Alto, Calif.) or the Oligonucleotide Synthesis Core Facility of the UAB Comprehensive Cancer Center, and their specificity was verified by means of RT-PCR on RNA extracted from mitogen-stimulated mouse spleen cells. After heating at 95° C. for 2 min, cDNA was amplified for 35 cycles consisting of: 45s at 94° C., 3 minutes at 72° C., and 2 minutes at 60° C. The products of amplification were analysed by 2% agarose gel electrophoresis, revealed by ethidium bromide staining, and photographed by UV transillumination. The results were scored according to the presence of a band of appropriate molecular size: −, no detectable band; ±, very faint or uncertain band; +, clearly detectable band; ++, very strong band.

EXAMPLE 13

Statistical Methods

Quantitative results were evaluated by Student's t test, by means of MultiStat (Biosoft, Ferguson Mo.) on a Macintosh computer. Antibody data were transformed logarithmically to normalize their distribution and homogenize the variances.

EXAMPLE 14

Antibody Responses

I.g. immunization of mice with SBR, SBR-CTA2/B, or SBR-CTA2/B plus CT incrementally induced serum IgG and salivary IgA antibodies measured against whole AgI/II (FIGS. 5A and 5B). Immunization with SBR alone resulted in weak but statistically significant (P<0.001 at all intervals) serum IgG antibody responses, and modest salivary IgA antibodies that were significantly elevated above background only after the second and third immunization (P<0.001 and P<0.01, respectively). Administration of the SBR-CTA2/B chimeric protein generated significantly greater serum IgG responses (P<0.001), and co-administration of CT as an adjuvant further enhanced both the level and the earlier development of serum IgG antibodies. Salivary IgA antibodies also tended to be elevated by immunization with SBR-CTA2/B chimeric protein especially when given with CT as adjuvant. However, because of variation between animals, statistical significance was attained only after 2 doses given with CT. Nevertheless, the general pattern of results was in accordance with expectations based on responses to AgI/II alone or chemically conjugated to CTB, and administered i.g. without or with CT adjuvant. Total salivary IgA concentrations also increased in all animals during the immunization period, from 2.13±0.61 µg/ml in unimmunized animals to 5.92±0.64 µg/ml after 3 immunizations, but there were no significant differences between the immunization groups.

EXAMPLE 15

T Cell Proliferative Responses

To show whether T cells capable of proliferating in vitro in response to stimulation with AgI/II had been induced by the first, second, or third i.g. dose, groups of 3 mice were killed 10 days after a first, second, or third immunization with each immunogen preparation, and mononuclear cells from PP, MLN, and spleens were cultured with or without AgI/II. Incorporation of $^3$[H]-thymidine expressed as stimulation indices revealed that AgI/II responsive cells were elicited in the lymphoid tissues associated with the intestine, incrementally with the number and form of the immunogen doses (FIG. 6). PP and MLN cells taken from mice given 2 or 3 doses of SBR or of SBR-CTA2/B alone showed modest proliferative responses to AgI/II in vitro (stimulation indices in the range 2.4–3.2; 5.44 for PP from mice given 3 doses of SBR-CTA2/B), whereas PP and MLN cells from mice immunized with SBR-CTA2/B plus CT adjuvant showed proliferative responses after one dose (stimulation indices 2.3 and 3.6, respectively), and greater responses after 2 or 3 doses (stimulation indices 3.1–6.1). The proliferative responses of PP and MLN cells were different: MLN cells responded similarly to (or less than) PP cells when taken from mice immunized with SBR or SBR-CTA2/B, but showed greater responses to AgI/II in vitro when taken from mice given AgI/II-CTA2/B plus CT. Spleen cells generally did not respond to stimulation with AgI/II in vitro (stimulation indices <2), except for those taken from mice immunized once with SBR-CTA2/B plus CT (stimulation index=2.8). Cells from the PP, MLN, or spleens of unimmunized mice did not proliferate in response to AgI/II in vitro (stimulation indices 1.2–1.5).

EXAMPLE 16

T Cell Surface Marker Analysis

To elucidate the nature of the T cell responses to i.g. immunization, cells freshly isolated from PP, MLN, spleen, or peripheral blood of mice immunized once, twice, or three times with the different immunogens were analyzed by flow cytometry for the proportion of cells expressing T cell markers CD3 (all T cells), CD4 (T helper phenotype), or CD8 (T suppressor/cytotoxic phenotype). The results are shown in FIG. 7. Among PP cells, there was an increase in the proportion of total T cells after each immunization that was most noticeable in animals immunized with SBR-CTA2/B or SBR-CTA2/B plus CT. This increase was mostly in the CD4$^+$ T helper population, whereas the CD8$^+$ T suppressor/cytotoxic population remained small. The MLN cell populations remained more stable, except in the case of cells from mice immunized with SBR-CTA2/B plus CT in which the CD4$^+$ population increased with the number of immunizations. MLN generally, however, contained more T cells of both phenotypes than PP, regardless of immunization status. Peripheral blood cells tended to show the greatest increases in the proportion of CD4$^+$ T cells after immunization, especially with SBR-CTA2/B plus CT, although these numbers must be interpreted with caution because of the small numbers of cells obtained. Spleen cells showed modest increases in the proportions of CD4⁺ T cells after immunization in all groups.

alone revealed type 1 (IFN-γ and IL-2) as well as type 2 (IL-4) cytokine responses upon stimulation in vitro, whereas cells from the same organs of mice immunized with SBR-CTA2/B chimeric protein revealed IL-4 but little or no type 1 cytokine response.

TABLE III

Cytokine expression in PP, MLN and spleen cell cultures of mice immunized with SBR, SBR-CTA2/B or SBR-CTA2/B + CT

| Immunization[a] | Culture[b] | IFN-γ | | | IL-2 | | | IL-4 | | | IL-5 | | |
|---|---|---|---|---|---|---|---|---|---|---|---|---|---|
| | | P | M | S | P | M | S | P | M | S | P | M | S |
| SBR | Control | –[c] | – | – | – | ± | – | ± | – | – | + | + | + |
| | +AgI/II | + | + | + | ++ | + | ++ | ++ | – | ++ | + | + | + |
| SBR-CTA2/B | Control | – | – | – | – | ± | – | + | ± | + | + | + | + |
| | +AgI/II | – | ± | + | – | + | ++ | + | + | ++ | + | + | + |
| SBR-CTA2/B + CT | Control | – | – | + | – | ± | + | ± | ± | + | + | + | + |
| | +AgI/II | – | + | ++ | – | ± | ++ | + | + | ++ | + | + | + |

[a]mice were immunized thrice at 10 day intervals and organs collected 3 days after the last immunization.
[b]cells were cultured in vitro for 24 hours without (control) and with AgI/II (0.1 ug/ml)
[c]cytokine mRNA expression detected by RT-PCR and scored according to the presence of ethidium bromide-stained band of appropriate molecular size;
–; no detectable band
±; very faint/uncertain band;
+, clear band; and
++, very strong band.
P = PP cell cultures,
M = MLN cell cultures;
S = spleen cell cultures.

EXAMPLE 17

Cytokine Expression

To elucidate the pattern of expression of cytokines, PP, MLN, and spleen cells were taken from mice immunized three times with SBR, SBR-CTA2/B, or SBR-CTA2/B plus CT 3 days after the last dose, cultured in vitro for 24 hours with or without AgI/II, and examined for the presence of mRNA for IFN-γ, IL-2, IL-4, IL-5, IL-6, and IL-10 by RT-PCR. After culture with AgI/II, PP, MLN, and spleen cells from mice immunized with SBR alone revealed mRNA for IFN-γ and IL-2, but only PP and spleen cells also revealed IL-4 mRNA, whereas IL-5 mRNA was detectable in all cell cultures regardless of stimulation (TABLE III). PP cells from mice immunized with SBR-CTA2/B, without or with CT adjuvant, did not reveal mRNA for IFN-γ or IL-2, even after culture with AgI/II, and MLN cells from these animals revealed variable IFN-γ and IL-2 mRNA responses. However, PP, MLN, and spleen cells revealed IL-4 mRNA particularly after stimulation with AgI/II, whereas all cultures were positive for IL-5 mRNA. Likewise, mRNA for IL-6 and IL-10 was found in all cell cultures, regardless of immunization or in vitro stimulation. There was an increase in IFN-γ and IL-2 expression (in response to stimulation with AgI/II in vitro) in PP, MLN, and spleen cells from mice immunized 3 times with SBR alone relative to cells from mice immunized twice. Likewise, spleen cells from mice immunized 3 times with SBR-CTA2/B (without or with CT) showed increased AgI/II-specific expression of IFN-γ, IL-2, and IL-4 relative to twice-immunized mice. Cells from unimmunized mice did not respond in culture with AgI/II by the expression of IFN-γ, IL-2, and IL-4 mRNA above that revealed in control cultures, except that spleen cells showed weak evidence of IFN-(expression on culture with AgI/II. Thus, PP and MLN cells from mice immunized with SBR Lymphocytes taken from the PP and MLN of mice immunized i.g. with SBR, or SBR-CTA2/B without or with CT as adjuvant were capable of proliferating in vitro when stimulated with AgI/II, showing a similar overall pattern of T cell responses to the different regimens and stages of immunization as the serum and salivary antibody responses. Immunization with SBR alone induced the lowest proliferative responses in PP and MLN cells, and this was reflected also in little change in the proportions of CD4⁺ and CD8⁺ T cells in these organs. Moreover, the pattern of cytokine expression in the cells from PP and MLN of these mice suggested a mixed type 1 and type 2 helper activity, possibly governed by Th0 cells. Coupling SBR to CTB in the form of the SBR-CTA2/B chimeric protein enhanced its immunogenicity with respect to T cell responses in PP and MLN, and the addition of CT as an adjuvant further elevated these responses. Furthermore, the cytokine expression pattern in PP and MLN cells from mice immunized with SBR-CTA2/B (with or without CT) indicated that T cell help was skewed towards Th2 activity. However, the finding of IL-5, IL-6, and IL-10 mRNA in cell cultures regardless of antigen stimulation in vitro is not readily explained in these terms, but may indicate constitutive expression of these cytokines or their continued expression ex vivo after immunization. It is also possible that Il-6 and IL-10 mRNA were derived from macrophages present in the cell cultures, although these would be largely adherent and unlikely to be harvested along with the lymphocytes.

The proportions of CD4⁺ T cells in PP increased after each additional dose of these immunogen preparations, but a corresponding increase was seen in MLN cells only from mice immunized with SBR-CTA2/B chimeric protein and CT adjuvant. The finding that these T cell responses occurred in PP and MLN as early as after the first immunization, at least with SBR-CTA2/B, showed that antigen-sensitized T cells were elicited before IgA antibody responses became elevated in the effector sites of mucosal immunity such as salivary glands. The responses in MLN and PP were different, as significant proliferative responses and increased proportions of CD4+ cells during the course of immunization were developed in MLN cells only when CT was used as an adjuvant, and moreover MLN from all mice contained higher proportions of T cells of both phenotypes than corresponding PP. The proportion of CD8+ cells was higher in MLN than in PP, but as it was not reduced by the administration of CT as an adjuvant, it appears that the enhanced AgI/II-specific proliferation in MLN cells from mice given CT is not due to inhibition of CD8+ suppressor cells by CT. The spleen, a non-mucosal lymphoid organ, displayed little or no response in terms of antigen-specific proliferating T cells, despite the considerable elevation of serum IgG antibodies especially when SBR-CTA2/B was given together with CT adjuvant. This is consistent with the relatively modest numbers of specific antibody-secreting cells found in the spleen after i.g. immunization with AgI/II chemically conjugated to CTB and given with CT. Throughout these experiments, although the mice were immunized with SBR or SBR-CTA2/B chimeric protein representing residues 186 to 577 of AgI/II, both antibody and T cell responses could be detected with intact AgI/II. This implies that SBR retains conformational structure similar to that of the corresponding part of the whole AgI/II molecule, and that both are processed similarly by antigen-presenting cells.

These responses are in accordance with the concept of the common mucosal immune system, and the dissemination of antigen-sensitized T and B cells from the inductive sites such as PP, through the MLN that drain the lymph flow from the small intestine, and thence into the circulation prior to relocating in the effector sites of mucosal immunity, including the salivary glands. Thus, i.g. immunization with SBR, especially when coupled to CTB in the form of a chimeric protein, leads to the appearance of antigen-responsive T cells in both PP and MLN. Because few cells were recoverable from blood, it was not practically possible to trace the appearance of such cells in the circulation, although this has been well documented in humans. The transient circulation of specific antibody-secreting cells, predominantly of the IgA isotype, approximately one week after mucosal immunization has been demonstrated in human and animal systems. Curiously, perhaps, it appears that the peak of circulating antigen-specific T cells occurs after the peak of circulating antibody-secreting cells, and an increased proportion of CD4+ T helper cells was found in the peripheral blood of mice 10 days after the second or third dose of SBR-CTA2/B, especially if CT was also given as an adjuvant. Cytokine-secreting T cells occur in effector sites of mucosal immunity, such as the salivary glands.

CT has been shown to enhance T helper responses in intestinal tissues, and particularly the Th2 subset that is held to promote high levels of serum IgG and mucosal IgA antibody responses. Type 2 cytokine production by antigen-specific T cells in nasal-associated lymphoid tissue and the draining cervical lymph nodes of mice immunized intranasally, as well as in PP and MLN of mice immunized i.g., with AgI/II conjugated to CTB were also found. CT is known to deplete selectively CD8+ intraepithelial lymphocytes and while the functions and migratory potential of these cells are incompletely understood, any such effect within inductive sites such as the PP would also serve to elevate the proportion of CD4+ T cells. However, although the proportion of CD8+ cells declined slightly in some tissues, this appeared to occur concomitantly with an increase in the number of CD3+ cells, in particular the CD4+ subset. Whether CTB itself can serve as an adjuvant in the absence of intact CT has been controversial. Synergism between CTB and CT has been demonstrated and most commercially available, non-recombinant preparations of CTB contain small amounts of intact CT that may be sufficient to show this effect. The genetically constructed SBR-CTA2/B chimeric protein, in which the toxic CTA1 subunit has been deleted, is clearly able to induce mucosal and circulating antibodies without the necessity for additional CT. The adjuvant activity of CT may be closely linked to its toxicity which is a function the ADP-ribosyltransferase activity of the A1 subunit. Adjuvanticity of the related $Escherichia$ $coli$ heat-labile enterotoxin can be dissociated from toxicity. Fusion proteins of CTB directly coupled to other antigenic peptides have been constructed, but the conformation of CTB and its ability to form $G_{M1}$-binding pentamers tend to be disrupted by peptides longer than approximately 12 amino acid residues and moreover, their mucosal immunogenicity seems to be limited in the absence of additional CT. These limitations do not apply to SBR-CTA2/B chimeric protein, in which a large 42 kDa segment of protein is fused to the CTA2 subunit which couples it noncovalently to the CTB pentamer to preserve its $G_{M1}$ ganglioside-binding activity. The enhanced enteric immunogenicity of SBR-CTA2/B chimeric protein, even in the absence of CT, is advantageous for an oral vaccine, as recombinant CTB has been shown to be a safe and effective immunogen in humans.

I.g. immunization with SBR, especially when genetically coupled to CTB to enhance both mucosal and circulating antibody responses, induces T cell responses in the gut-associated lymphoid tissues such as PP and MLN. Furthermore, these T cell responses occur after one or two doses of immunogen, earlier than the antibody responses, and include increased proportions of CD4+ T helper cells. The responses are enhanced by, but are not dependent upon, the addition of CT as an adjuvant.

EXAMPLE 18

Expression of SBR in $S.$ $typhimurium$

The pac gene segment encoding the SBR region (1.2 kilobases [kb]) was removed from pSBR-CT$^{AA1}$ by restriction digestion with the NcoI and XhoI endonucleases, and purified after agarose gel electrophoresis of the digest and extraction using the QIAEX gel extraction kit (Qiagen, Chatsworth, Calif.). The pET20b(+) expression vector (3.7 kb; Novagen, Madison, Wis.) was similarly digested by NcoI and XhoI, dephosphorylated by calf intestinal alkaline phosphatase and purified by gel extraction. The pac segment was then ligated into pET20b(+) in frame with the 3' end of the pelB leader sequence (required for the transport of cloned polypeptides into the periplasm) and the resulting ligation product, designated pSBR, was introduced into $S.$ $typhimurium$ BRD509 (pGP1-2) (6) by means of electroporation using a gene pulser (Biorad, Richmond, Calif.) set at 2.5 kV, 25 µF, and 200 Ohms. Transformed colonies were selected on L-agar plates (1% tryptone, 0.5% yeast extract, 1% NaCl, 0.1% dextrose, 1.5% agar) supplemented with 50 µg/ml carbenicillin and 50 µg/ml kanamycin (to select for pSBR and pGP1-2, respectively). Transformants were examined for the presence of two plasmids with sizes of 4.9 and 7.2 kb, corresponding to the size of pSBR and pGP1-2, respectively. Both plasmids were required for the expression of SBR since its transcription in pSBR is under the control of the bacteriophage T7 promoter and pGP1-2 provides a source of T7 RNA polymerase. Expression of the SBR polypeptide in transformants containing both plasmids was induced at mid-log phase by a shift from 30° C.–37° C., and production of SBR was confirmed by western immunoblotting of cell lysates using antibodies to the native AgI/II molecule (FIG. 8B). Target gene induction in this system is temperature-regulated because the T7 RNA polymerase is under the control of the 1 $P_L$ promoter that is regulated by the cI857 temperature-sensitive 1 repressor (FIG. 8A).

EXAMPLE 19
Estimation of Recombinant Protein Production

To determine the amount of the SBR polypeptide produced by S. typhimurium (pGP1-2+pSBR-$CT^{AA1}$) (6) and S. typhimurium (pGP1-2+pSBR) (FIG. 8B), a calibrated "sandwich" ELISA standardized with purified rSBR was performed using cell lysates obtained by sonication. This quantitative ELISA was repeated four times using independent cultures which were grown at 30° C. and subsequently processed for the immunizations (see "Immunizations" below). The construction of standard curves and the interpolation of the unknowns was performed by means of a computer program based on four-parameter logistic algorithms (Softmax/Molecular Devices, Menlo Park, Calif.). For the ELISA, rabbit anti-mouse IgG followed by a mouse monoclonal IgG antibody to SBR served as the coating reagents while peroxidase-conjugated rabbit polyclonal antibodies to native AgI/II was used for detection of bound protein. SBR used as standard was purified from cell lysates by metal-chelation chromatography on a nickel-charged column (Novagen), according to the manufacturer's instructions. The affinity of SBR for nickel arises from a 6-residue histidine sequence (at its C-terminal end) which was derived from the pET-20b(+) expression vector. Recovery of SBR from the column was achieved by elution with imidazole. The purity of the SBR preparation was verified by SDS-PAGE and its protein content was estimated by the bicinchoninic acid protein determination assay (Pierce, Rockford, Ill.) using BSA.

A similar approach was used to quantify the SBR-$CT^{AA1}$ chimeric protein with the exception that the plates were coated with $G_{M1}$ ganglioside (Calbiochem, La Jolla, Calif.). This $G_{M1}$-ELISA was standardized with SBR-$CT^{AA1}$ purified. Briefly, the chimeric protein was isolated from whole-cell extracts by size-exclusion chromatography on a Superose 12 HR 16/50 column (Pharmacia-LKB, Piscataway, N.J.) followed by anion-exchange chromatography on a Mono Q column (Pharmacia-LKB). Results are expressed as %SBR or SBR-$CT^{AA1}$ per total soluble protein in the lysates.

EXAMPLE 20
Immunizations

Overnight cultures of recombinant S. typhimurium BRD509 expressing SBR-$CT^{AA1}$ or SBR were diluted 1:100 in L-broth containing 50 µg/ml of kanamycin and 50 µg/ml of carbenicillin and grown at 30° C. with shaking and aeration until $A_{600nm}$ reached 0.5–0.55. The bacteria were recovered by centrifugation and resuspended in a medium consisting of 4 parts Hank's balanced salt solution (Life Technologies Inc., Grand Island, N.Y.) and 1 part sodium bicarbonate (7.5% solution; Mediatech, Washington, D.C.). The number of bacteria in the suspension was estimated by extrapolating from a growth curve and was confirmed by plating dilutions of the bacterial inoculum on L-agar plates (with or without the appropriate antibiotics) and enumerating the colonies grown after overnight incubation at 30° C.

BALB/c mice, 10 to 12 weeks old, from a pathogen-free colony, were used for oral and i.n. immunization studies performed according to NIH guidelines and protocols approved by the UAB Institutional Animal Care and Use Committee. An oral dose containing $10^9$ CFU in 0.25 ml was administered to groups of 5–6 mice by intragastric (i.g.) intubation using a 22-gauge feeding tube (Popper and Sons Inc., Hyde Park, N.Y.) The mice were immunized 1 to 3 times in a period of 6 days. A single booster immunization with $10^{10}$ CFU was given 15 weeks later. For i.n. immunizations, groups of 6 mice were inoculated 3 times (in a period of 6 days) with $10^8$ CFU in a volume of ~20 µl which was slowly applied in the external nares by means of a micropipettor. A single booster i.n. immunization with $10^9$ CFU was performed 15 weeks later. In another experiment, groups of 3 mice received a single primary immunization ($10^{10}$ CFU for i.g. or $10^9$ CFU for i.n. delivery) followed by a booster immunization with the same dose 15 weeks later. An age-matched, unimmunized control group consisting of 5 mice was also included to monitor background antibody levels during the course of the studies.

EXAMPLE 21
Sampling and Quantification of Antibody Responses

Serum was obtained by centrifugation of blood samples collected from the lateral tail vein with heparinized capillary pipettes. Preimmune samples were obtained 1 day before the immunizations and subsequent to immunizations collections were made 3, 5, and 7 weeks later, one day before the booster immunization (week 15), and at biweekly intervals thereafter (weeks 17 and 19). Saliva samples were collected at the same times as serum by means of a pipettor fitted with a plastic tip after stimulation of salivary flow by i.p. injection of 5 µg carbachol (Sigma Chemical Company, St. Louis, Mo.). Fecal extracts were prepared by vortexing 3 fecal pellets from each mouse in 600 µl extraction buffer (PBS containing 0.02 % azide, 1% BSA, 1 mM PMSF, and 5 mM EDTA). The extracts were subsequently centrifuged and the supernatants obtained were assayed for total IgA levels (see below) and were adjusted to contain 100 µg of total IgA per ml ("standardized" fecal extracts) by adding an appropriate volume of extraction buffer.

The levels of isotype-specific antibodies from serum, saliva, or fecal extracts, and total salivary or intestinal IgA were determined by ELISA on microtiter plates coated with native AgI/II (chromatographically purified from S. mutans culture supernatants), $G_{M1}$ followed by CT (List Biological Laboratories, Campell, Calif.), formalin-killed cells of S. typhimurium BRD509, or goat anti-mouse IgA. The plates were developed with the appropriate peroxidase-conjugated goat anti-mouse Ig isotype (IgG for serum samples and IgA for secretion samples) and o-phenylenediamine substrate with $H_2O_2$. IgG 1 or IgG2a antibody responses were assayed using peroxidase-conjugated IgG subclass-specific antibodies. All antibodies used for ELISA were purchased from Southern Biotechnology Associates, Inc., Birmingham, Ala. The concentration of antibodies/total Ig in test samples was calculated by interpolation on standard curves generated using a mouse Ig reference serum (ICN Biomedicals, Costa Mesa, Calif.) and constructed by a program based on four parameter logistic algorithms (Softmax/Molecular Devices).

EXAMPLE 22
Statistical Analysis

Results were evaluated by Student's t test by means of the Multistat program (Biosoft, Cambridge, UK) on a Macintosh computer. Differences were considered significant at the $P<0.05$ level. antibody data were logarithmically transformed to normalize their distribution and homogenize the variances. The data were finally retransformed and presented as geometric means x/÷ SD.

EXAMPLE 23
Recombinant Protein Production by the Salmonella Clones

Using a "sandwich" ELISA calibrated with purified rSBR, it was determined that *S. typhimurium* (pGP1-2+pSBR-CT$^{AA1}$) and *S. typhimurium* (pGP1-2+pSBR) produced similar amounts of the SBR polypeptide (Table IV). Slightly higher levels of SBR were detected in the lysates from the pSBR-containing clone than in the extracts from the clone expressing the SBR-CT$^{AA1}$ chimeric molecule, but the difference was not statistically significant. This might have resulted from the presence of CTA2/B which could sterically interfere with the recognition of the SBR component of the chimeric protein by the antibodies used in the "sandwich" ELISA. As expected, $G_{M1}$-ELISA calibrated with purified SBR-$CT^{\Delta A1}$ detected a $G_{M1}$-binding protein possessing SBR epitopes only in lysates from the pSBR-$CT^{\Delta A1}$-containing clone (TABLE IV). The expression level of SBR-$CT^{\Delta A1}$ in the lysates was approximately 2–3% of the total soluble protein (TABLE IV). These results validate the appropriateness of comparing the capacity of these two clones to induce antibody responses to the SBR of AgI/II.

Analysis of serum samples obtained from i.n. immunized mice for anti-AgI/II responses, confirmed the trend of higher responses in mice immunized with *S. typhimurium* expressing SBR than SBR-$CT^{\Delta A1}$ seen in i.g. immunized animals (FIG. 11A). In this case the differences in anti-AgI/II responses between the clones were statistically significant except for the responses on week 17 (FIG. 11A). This trend did not seem to correlate with the anti-Salmonella responses induced by i.g or i.n. immunization. In fact, the anti-vector responses appeared to be higher for the SBR-$CT^{DA1}$-producing clone; FIGS. 10A and 11B. The kinetics as well as the magnitude of the serum IgG responses to Salmonella and the cloned Ags after i.n. immunization (FIGS. 11A and 11B) were comparable to those after i.g. immunization (FIGS. 9A, 9B, 9C and 10A) despite that the number of Salmonellae given by the i.n. route was lower by one order of magnitude.

In the above experiments, preimmune serum samples (from 10- to 12-week old mice) did not contain detectable antibodies to AgI/II, CT, or Salmonella (corresponding data points at week 0 in FIGS. 9A, 9B, 9C, 10A, and 11A and 11B, represent the detection limit of the ELISA). Furthermore, 27 week-old unimmunized controls did not show substantial antibody levels to AgI/II or CT (≦1.2 μg/ml) but they did develop a relatively weak response (compared to immunized animals) against Salmonella (17.8×/÷1.6 μg/ml, n=5), probably because of cross-reactions with related gram-negative bacteria of their normal flora.

TABLE IV

Production of recombinant protein by *S. typhimurium* (pGP1-2 + pSBR and *S. typhimurium* (pGP1-2 + pSBR-$CT^{\Delta A1}$)clones

| Assay: | Elisa Method: Coating | Elisa Method: Develop. | Exp. | Protein Amount[a]: pSBR | Protein Amount[a]: pSBR-$CT^{\Delta A1}$ |
|---|---|---|---|---|---|
| SBR | SBR-MAb | AgI/II-PAb | No. 1 | 1.68 | 1.18 |
| | | | No. 2 | 1.33 | 1.23 |
| | | | No. 3 | 1.51 | 1.07 |
| | | | No. 4 | 1.13 | 1.14 |
| | | | Mean ± SD | 1.39 ± 0.21 | 1.16 ± 0.07 |
| SBR-$CT^{\Delta A1}$ | Gm1 | AgI/II-PAb | No. 1 | 0** | 2.03 |
| | | | No. 2 | 0 | 3.05 |
| | | | No. 3 | 0 | 3.49 |
| | | | No. 4 | 0 | 2.13 |
| | | | Mean ± SD | 0 | 2.68 ± 0.71 |

[a]amount of recombinant protein in cell lysate of clones containing either pSBR or pSBR-$CT^{\Delta A1}$;
* = % SBR polypeptide/total soluble protein in cell lysates;
** = % SBR-$CT^{\Delta A1}$ chimeric protein/total soluble protein in cell lysates.

EXAMPLE 24

Serum IgG Antibody Responses

Oral immunization of mice with the *S. typhimurium* clones expressing SBR or SBR-$CT^{\Delta A1}$ resulted in dose-dependent primary serum IgG responses to AgI/II which were significantly enhanced after a single booster dose (FIG. 9A). Although the responses to AgI/II induced by i.g. administration of either *S. typhimurium* clone (i.e., expressing SBR alone or linked to CTA2/B) were not statistically different, a trend was observed towards higher serum IgG responses after two or three primary immunizations with *S. typhimurium* expressing SBR alone than with the clone expressing the SBR-$CT^{\Delta A1}$ chimeric protein (FIGS. 9B and 9C).

The response to the Salmonella vector was essentially similar with increasing number of doses (one to three) given during primary immunization (data shown for the groups which received two primary doses; FIG. 10A). As expected, serum IgG antibodies to CT were induced after immunization with the clone expressing the chimeric SBR-$CT^{\Delta A1}$ molecule but not with the clone expressing SBR alone (FIG. 10A). As with anti-AgI/II responses, the serum IgG response to CT was also significantly elevated following the booster immunization (FIG. 10A).

In these studies antibody responses to the SBR of AgI/II were detected using native AgI/II as the coating agent in the ELISA, as recombinant vaccines should be able to induce responses against the antigen expressed by the pathogen. On a limited number of samples, the influence of coating with purified rSBR on the magnitude of the detected responses was also determined. ELISA with serum samples tested on plates coated with either rSBR or AgI/II showed that the antibody response to rSBR was about 2 times higher than to AgI/II (2.15×/÷1.49, n=13), implying substantial antigenic and possibly structural similarities between rSBR and the corresponding region (residues 186 to 577) of the whole AgI/II. Moreover, the antibody response against the CTA2/B component of the chimeric protein was about 3 times higher (3.34×/÷1.10, n=6) when detected with native CT bound to $G_{M1}$ ganglioside-precoated plates than when CT was directly coated on microtiter plates.

EXAMPLE 25
IgG2a/IgG1 Profile for Vector and Carried Antigens

To determine the subclass distribution of serum IgG antibody responses, samples from mice orally immunized with SBR-CT$^{\Delta A1}$-expressing *S. typhimurium* were analyzed for levels of IgG2a and IgG1 antibody responses which are indicative of a Th type-1 or Th type-2 response, respectively. Serum IgG antibodies to whole Salmonella belonged predominantly to the IgG2a subclass (IgG2a/IgG1>10) but a mixed IgG2a and IgG1 response pattern (IgG2a/IgG1≈1) was observed for the cloned Ags, SBR and CTA2/B (TABLE V). Analysis of samples from a study in which mice were orally immunized with purified SBR-CT$^{\Delta A1}$, revealed predominant IgG1 responses to SBR and CTA2/B, indicating that immunization with the *S. typhimurium* vector shifted the responses towards the IgG2a subclass (TABLE V). In the case of the anti-SBR responses the shift was statistically significant. In terms of the IgG2a/IgG1 ratio, the response to SBR was not influenced by the route of immunization (i.g. or i.n.) or the presence or absence of CTA2/B (clones expressing SBR-CT/($^{A1}$ or SBR alone).

TABLE V

Profile of IgG2a/IgG1 antibody responses in serum after oral immunization with SBR-CT$^{\Delta A1}$ expressed in *S. typhimurium* or administered as purified immunogen

| Immunization with | antibody response to: | IgG2a/IgG1* | No. of mice IgG2a/IgG>1 |
|---|---|---|---|
| *S. typhimurium* vector (n = 16) | SBR | 1.02 ± 2.26** | 8/16 |
| | BTA2/B | 1.21 ± 2.6 | 10/16 |
| | Salmonella | 11.2 ± 2.21 | 16/16 |
| Purified SBR-CT$^{\Delta A1}$ (n = 6) | SBR | 0.3 ± 1.94 | 0/6 |
| | CTA2/b | 0.48 ± 1.73 | 1/6 |

\* = ration obtained following quanfication of subclass-specific antibody levels
\*\* = values are the geometric mean x/(SD of the IgG2a/IgG1 ratios of individual mice.

EXAMPLE 26
Salivary IgA Antibody Responses

Oral immunization of mice with recombinant Salmonella vector, one to three times, resulted in the induction of increasingly higher salivary IgA antibody responses to AgI/II (FIGS. 12A, 12B, and 12C). A single oral booster immunization resulted in augmented antibody levels in the groups immunized one or two times during priming, whereas the secondary response in the groups immunized three times for priming was slightly lower than the peak primary response at the time measured (FIG. 12C). All groups of mice displayed significantly higher antibody levels four weeks after the secondary immunization than immediately before the booster immunization. Interestingly, although the anti-AgI/II responses induced by the SBR- and the SBR-CT$^{\Delta A1}$-expressing clones were generally not significantly different (except for the responses of the groups immunized three times for primary immunization where differences reached statistical significance after the boosting (FIG. 12C)), they showed the opposite trend than that observed in the serum IgG responses, i.e., the presence of CTA2/B appeared to enhance the salivary IgA response to AgI/II. In contrast, the salivary IgA anti-vector responses induced by the two Salmonella clones were very similar (data shown for the groups which were given two primary doses; FIG. 10B). IgA antibodies to CT in saliva were detected after immunization with the SBR-CT$^{\Delta A1}$-expressing clone only, and were significantly elevated by secondary immunization (FIG. 10B). The salivary IgA responses to Salmonella and the cloned Ags after i.n. administration of the recombinant *S. typhimurium* (FIGS. 13A, 13B and 13C) displayed similar characteristics as after i.g. immunization and were comparable in magnitude despite the use of lower doses. The secondary response to CT and AgI/II reached significantly higher levels than the primary response, two and four weeks following the booster immunization, respectively. When saliva samples were normalized for total IgA content, samples from 27-week-old unimmunized mice showed similar levels of "background" antibody activity to the test Ags as the pre-immune samples of immunized animals reported in FIGS. 10B, 12A, 12B, 12C, 13A, 13B, and 13C.

The finding that anti-AgI/II responses tended to be higher in saliva but lower in serum when mice were immunized with the SBR-CT$^{\Delta A1}$-expressing clone than with the clone producing SBR alone, was further supported by data from additional groups of mice. These mice were given a single immunization of $10^{10}$ CFU by the i.g. or $10^9$ CFU by the i.n. route, boosted with the same dose 15 weeks later, and displayed the above mentioned trend regardless of the route of administration (FIGS. 14A and 14B). In the same experiment, the mice immunized with a single i.g. dose of $10^{10}$ CFU showed higher anti-AgI/II responses in serum and saliva than mice which received a single i.g. dose of $10^9$ CFU (FIGS. 9A and 12A), but equal or slightly lower responses than mice given 3 i.g. doses of $10^9$ CFU (FIGS. 9C and 12C).

EXAMPLE 27
Intestinal IgA Responses

IgA anti-AgI/II responses were also detected in fecal extracts from i.g. immunized mice (FIGS. 15A, 15B, and 15C). The kinetics of the responses induced by the two recombinant *S. typhimurium* clones also showed some trend for higher anti-AgI/II responses when the SBR antigen was co-expressed with CTA2/B (FIGS. 15A, 15B, and 15C). This trend was less pronounced than seen in saliva (FIGS. 12A, 12B, and 12C), and it did not show statistical significance except for two time points, i.e., FIG. 15A, at week 15 with groups given 1 primary dose, and, FIG. 15B, at week 19 with groups given 2 primary doses. At the same time, the anti-Salmonella response appeared to be higher in the case of the clone producing SBR alone (FIG. 10C), suggesting that the relatively high anti-AgI/II responses in the case of the SBR-CT$^{\Delta A1}$ clone may be related to the co-expression of SBR and CTA2/B. Intestinal IgA responses to Salmonella and the cloned Ags were also induced after immunization by the i.n. route (FIGS. 16A and 16B). As in the case of saliva, fecal samples from 27 week-old unimmunized mice showed similar levels of "background" antibody activity against the test Ags with the preimmune samples of immunized animals, but the background activity against CT appeared to be higher compared to that against AgI/II or even Salmonella (FIGS. 10C, 15A, 15B, 15C, 16A, and 16B).

Using a temperature-regulated expression system engineered in avirulent *S. typhimurium*, the present invention demonstrated high levels of antibodies against the cloned heterologous Ags in serum and mucosal secretions after oral or i.n. immunization. Expression of recombinant immunogens in this system was activated under in vivo conditions (37° C.), since at 37° C. target protein induction was shown to be optimal. This system was used to investigate whether the non-toxic A2/B moiety of cholera toxin can act as a Salmonella-cloned adjuvant when co-expressed with the SBR protein antigen. For this purpose, a *S. typhimurium* clone expressing SBR alone and a similar clone expressing the SBR-CT$^{\Delta A1}$ chimeric protein were used, which were found to produce similar levels of the SBR polypeptide. The amount of chimeric protein produced by the SBR-CT$^{\Delta A1}$ clone (2.68% of total soluble protein) was consistent with the estimated SBR levels (1.16%) expressed by the same clone, since SBR comprises 39% of the whole chimeric molecule by weight.

Quantitative analysis of serum samples showed that the IgG responses to SBR were generally lower after immunization with the SBR-CT$^{AA1}$-expressing *S. typhimurium* than with the clone expressing SBR alone. Although this may suggest intramolecular antigenic competition as observed within the IgG molecule, i.e., higher responses are induced to the Fab fragment when Fab is injected alone than when the whole IgG molecule is used for immunization, analysis of responses in secretions revealed an opposite trend. Comparing the mucosal IgA antibody levels to AgI/II induced by immunization with the two *S. typhimurium* clones at each time point examined (56 time-points including all groups from both i.g. and i.n. immunization; FIGS. 12A, 12B, 12C, 13B, 14B, 15A, 15B, 15C, 16A, and 16B), the response in the case of the clone expressing SBR linked to CTA2/B was higher on 51 occasions (91%). In contrast, the serum IgG response was higher in 83% of the occasions (31/36) in the case of the other clone, i.e., the one expressing SBR alone (FIGS. 9A, 9B, 9C, 11B, and 14A). One can speculate that CTA2/B may have a dual influence on anti-SBR responses arising from its dual role as an immunogen and as an immunoenhancing agent. As an immunogenic component of the SBR-CT$^{AA1}$ chimeric molecule, CTA2/B may tend to depress the immune response to SBR through antigenic competition, and as a mucosal adjuvant it may tend to potentiate anti-SBR responses. This dual effect might have differentially influenced the observed mucosal and systemic responses if CTA2/B is able to provide better help for antibody production in mucosal inductive sites than in systemic compartments. Presumably, Salmonella-expressed CTA2/B can be delivered to both mucosal and systemic inductive sites because of the ability of the vector to colonize mucosal lymphoid tissues and to disseminate to systemic tissues. Interestingly, in an immunization study with influenza virus administered mucosally or systemically in the absence or presence of CTB, the adjuvant effect of CTB on antiviral antibody responses was found to be more pronounced after i.n. than after subcutaneous or i.p. immunization. These findings cannot be attributed to quantitative differences (equal doses were given by all routes and in the case of i.n. immunization the amount actually absorbed may be even less than that injected for systemic administration) but rather to a CTB adjuvant effect which is possibly influenced by the particular microenvironment where CTB acts.

Th1 or Th2 cells induce antigen-specific B cells to selectively produce IgG2a or IgG1 antibodies, respectively. Salmonella (as well as other intracellular microorganisms) generally induces a Th1-type response characterized by high levels of IFN-$\gamma$ and IgG2a antibodies. The serum IgG response to the *S. typhimurium* vector displayed a high (>10) IgG2a/IgG1 ratio. Moreover, a mixed IgG2a and IgG1 response (IgG2a/IgG1≈1) was induced against Salmonella-expressed SBR, although a predominant IgG1 response to SBR was observed after oral immunization with purified SBR-CT$^{AA1}$. These data also suggest that the type of response to a Salmonella-delivered protein antigen was not entirely determined by the vector but is also influenced by inherent properties of the cloned antigen.

The mechanisms for inducing intestinal IgA responses to orally administered vaccines have been extensively studied. Although less is known regarding responses induced after i.n. immunization, several mechanisms can be offered for the observed intestinal IgA responses following i.n. administration of recombinant Salmonella in mice. Antigenic stimulation of the nasal-associated lymphoid tissues which show anatomical similarities with the Peyer's patches in the gut (e.g., lymphoid follicles covered by M cells) may result in the dissemination and homing of lymphoid cells to remote mucosal effector sites, including the intestinal lamina propria, in a fashion analogous to stimulation of the GALT. Moreover, a portion of the Salmonella inoculum may have been swallowed by the mice resulting in direct stimulation of the GALT. To minimize this possibility, a relatively small volume was slowly applied to the external nares (~10 $\mu$l per nostril). If these mice did swallow some Salmonella organisms, the number would be relatively small compared to the oral dose given to i.g. immunized mice, i.e., 10 times higher than the i.n. dose. Alternatively, *S. typhimurium* could access the GALT by dissemination from nasal lymphoid tissues. Immunization by the i.n. route was generally as effective as by the i.g. route, despite using lower doses.

Besides a remarkable secondary IgG response in serum against AgI/II and CT, a pronounced secondary salivary IgA response was induced against the cloned Ags after i.n. and i.g. (especially when two primary doses were given) immunization, suggesting induction of immunological memory. Enhanced salivary IgA anamnestic responses to SBR or CTA2/B were not observed previously in mucosal immunization experiments using purified SBR-CT$^{AA1}$ or the whole AgI/II molecule chemically conjugated to native CTB. Because of concerns regarding the efficacy of repeated use of Salmonella as a carrier for various heterologous Ags, it was of interest that boosting of mucosal IgA and serum IgG antibody responses was induced after i.g. booster immunization of mice with a pre-existing intestinal IgA response to the Salmonella vector.

In summary, despite the requirement for genetic coupling of CTA2/B to SBR to induce substantial anti-SBR responses after mucosal immunization with purified immunogen, expression of SBR alone in an avirulent *S. typhimurium* vector was sufficient to induce high levels of antibodies in serum and mucosal secretions. The finding that the immunogenicity of Salmonella-delivered SBR was not significantly dependent on co-expression of CTA2/B, suggests that in oral immunization with purified SBR-CT$^{AA1}$ targeting of SBR to the GALT via $G_{M1}$ receptors on the overlying antigen-sampling M cells, may constitute an important immunoenhancing mechanism. The requirement for this mechanism, which would also reduce the exposure of SBR to proteases in the gut lumen, is bypassed by the Salmonella vector because of its tropism for the GALT, where SBR will eventually be delivered. The current system can be modified so that CTA2/B can find application as a Salmonella-cloned adjuvant, especially for Ags that are poor immunogens when delivered by this live antigen-delivery system.

EXAMPLE 28

Intranasal Immunization of Rats with AgI/II, AgII, and SBR Chemical/Genetic Conjugates Fischer rats, 19 days old, were used for intranasal immunization studies performed according to NIH guidelines and protocols approved by the UAB Institutional Animal Care and Use Committee. The animals were immunized 3 times at 14-day intervals with 50 $\mu$g of the appropriate inununogen (see group designations), with or without an adjuvant amount (1 $\mu$g) of cholera toxin (CT), in a volume of 50 $\mu$l which was slowly applied in the external nares by means of a micropipettor.

For sampling and quantification of antibody responses, serum was obtained by centrifugation of blood samples collected from the retroorbital plexus with heparinized capillary pipettes. Saliva samples were collected by means of a Pasteur pipette after stimulation of ovary flow by intraperitoneal injection of 10 μg carbachol. Samples were obtained 1 day before the immunizations and 2 weeks after the last immunization. The levels of isotype-specific antibodies from serum and saliva, and total salivary IgA were determined by ELISA on microtiter plates coated with native AGI/II, recombinant SBR, AgII, $G_{MI}$ followed by CT, or goat anti-rat IgA. The plates were developed with the appropriate peroxidase-conjugated goat anti-rat immununoglobulin isotype (IgG for serum samples and IgA for saliva samples) and o-phenylenediamine substrate with $H_2O_2$. The concentration of antibodies/total immunoglobulin in test samples was calculated by interpolation on standard curves generated using a rat immunoglobulin reference serum and constructed by a computer program based on four parameter logistic algorithms.

The results that follow are presented as μg/ml of specific serum IgG antibody or as % specific salivary IgA antibody/total IgA. Antibody data were logarithmically transformed to normalize their distribution and homogenize the variances. The data were finally retransformed and presented as geometric means x/+ standard deviation for ease of interpretation. The presented data are from samples obtained 2 weeks after the last immununization. Specific antibodies in preimmunune samples were not detectable.

Immunization groups 1, 2, and 3 are controls, groups 4 and 5 were immunized with SBR-CTA2/B chimeric protein (SBR-CT$^{AA1}$, shown as CHIM) without (group 4) or with (group 5) CT as adjuvant, and groups 6–11 were immunized with chemical conjugates of SBR, AgII, or AgI/II coupled to recombinant CTB, without or with CT as an adjuvant.

Antibody responses were assayed against the intact AgI/II (FIGS. 17 and 21), as well as against SBR (FIGS. 18 and 22), and AGII (another part of AGJM distinct from the part containing SBR; FIGS. 19 and 23). Responses against CT (FIGS. 20 and 24) are given for comparison, since the immunogens as well as the adjuvant (CT) where used also induce responses to CT. Since CT is regarded as the most potent mucosal immunogen, these comparisons serve to put the magnitude of responses to SBR or Ag I in perspective.

In all instances, responses (measured against SBR, AgI/II, or AGII) to the various immunogens given without CT adjuvant were undetecable; the use of CT as adjuvant was necessary to obtain responses in these rats (Fischer strain). This finding is in marked contrast to all previous results obtained in mice (BALB/c strain), in which antibody responses to SBR-CTA2/B chimeric protein or to AgI/II conjugated chemically to rCTB given intranasally were generated in the absence of CT adjuvant. The reason for this difference of response is not clear, and it is not known if this reflects the particular strain of rat used, or is typical of rats as compared to mice. Reports of studies performed on human subjects indicate that humans respond well to intranasal or oral immunization with recombinant CTB, i.e., more like mice than rats. The following is a comparison of responses to the different immunogens for animals immunized with CT as adjuvant.

Both SBR (in the form of either the chimeric immunogen, group 5; or the chemical conjugate, group 7) and AGII (group 9) as well as the intact AgI/II (group 9) induced antibodies detectable against AgI/II in serum (IgG, FIG. 17) and in saliva (IgA, FIG., 21). The intact AgI/II and AgII (serum only) tended to induce the strongest responses measured in this way. However, SBR (in either form) induced the strongest responses measurable against SBR (FIGS. 18 and 22) whereas AgII failed to induce responses to SBR. Conversely, AgII induced responses measurable against AgII (FIGS. 19 and 23) but SBR did not. Despite the fact that the use of CT as an adjuvant also induced very strong responses to itself (FIGS. 20 and 24), the responses to SBR, AgI/II, and AgII compare well with the responses to CT.

Therefore, the chimeric immunogen, SBR-CTA2/B, is very effective for inducing serum IgG and salivary IgA antibodies to SBR, which also react with the parent antigen, AgI/II. This may be advantageous, because SBR was selected as a part of the, AgI/II molecule that appears to be functionally important for the adherence of *Streptococcus mutans* to tooth surfaces. Immunization with AgI/II appears to induce antibodies most strongly against the AgII part of the molecule, yet earlier work indicated that antibodies to AgII might not be protective against *S. mutans*-induced dental caries. The advantage of using genetically constructed chimeric immunogens may therefore include the ability to direct an antibody response to a functionally important part of tbe antigen molecule that is otherwise less immunogenic than parts of the the molecule that may be functionally less important. Such a finding may be of considerable importance in vaccine development, since surface molecules of microorganisms that have functional activity in pathogenesis may have evolved structures that divert host immune responses away from the more sensitive parts of the molecule.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of producing an immune response by administration of an attenuated strain of bacteria, wherein said attenuated bacteria express an antigen of interest as a fusion protein from a plasmid which comprises in operable linkage:
    a) an origin of replication;
    b) a promoter; and,
    c) DNA sequences encoding the antigen of interest, wherein said DNA sequences are fused in frame to the A2 subunit of cholera toxin.

2. The method of claim 1, wherein salivary binding protein (SBR) from *Streptococcus mutans* surface protein (Ag I/II) is the antigen of interest fused to the A2 subunit of cholera toxin.

3. The method of claim 1, wherein said plasmid further comprises DNA sequences encoding subunit B of cholera toxin for coexpression with said fusion protein to facilitate assembly of a chimeric protein.

4. The method of claim 3, wherein said plasmid is pCT$^{AA1}$.

5. The method of claim 3, wherein salivary binding protein (SBR) from *Streptococcus mutans* surface protein (Ag I/II) is the antigen of interest fused to the A2 subunit of cholera toxin.

6. The method of claim 5, wherein said plasmid is pSBR-CT$^{\Delta\Delta 1}$ (alternatively designated pSBR-CTA2/B).

7. The method of claim 3, wherein said attenuated bacterial strain is administered by a route selected from the group consisting of orally, intranasally, intrarectally, intravaginally, intramuscularly, and subcutaneously.

8. The method of claim 3, wherein said immune response results in the production of antibodies to the protein antigen sequence in a bodily fluid selected from the group consisting of saliva, intestinal secretions, respiratory secretions, genital secretions, tears, milk and blood.

9. The method of claim 3, wherein said immune response is selected from the group consisting of development of antigen-specific T cells in the circulation and tissues of said individual, the development of cytotoxic T cells and immunological tolerance to the protein antigen sequence.

10. An attenuated Salmonella strain, wherein said Salmonella strain expresses a chimeric fusion protein from a plasmid which comprises in operable linkage:
   a) an origin of replication;
   b) a promoter;
   c) DNA sequences encoding a fusion protein of the antigen of interest fused in frame with the A2 subunit of cholera toxin; and,
   d) DNA sequences encoding subunit B of cholera toxin for coexpression with said fusion protein of the antigen of interest and A2 cholera toxin subunit to facilitate assembly of a chimeric protein.

11. An attenuated Salmonella strain, wherein said Salmonella strain expresses a chimeric fusion protein from a plasmid which comprises in operable linkage:
   a) an origin of replication;
   b) a promoter;
   c) DNA sequences encoding a fusion protein of salivary binding protein (SBR) from *Streptococcus mutans* surface protein (AgI/II) fused in frame to the A2 subunit of cholera toxin; and,
   d) DNA sequences encoding subunit B of cholera toxin for coexpression with said fusion protein of saliva binding protein and A2 cholera toxin subunit to facilitate assembly of a chimeric protein.

* * * * *